United States Patent [19]
Bolle et al.

[11] Patent Number: 6,060,543
[45] Date of Patent: May 9, 2000

[54] STABILIZER COMBINATION

[75] Inventors: Thomas Bolle, Efringen-Kirchen, Germany; Pascal Hayoz, Marly, Switzerland

[73] Assignee: Ciba Specialty Chemicals Corporation, Tarrytown, N.Y.

[21] Appl. No.: 08/925,014

[22] Filed: Sep. 8, 1997

[30] Foreign Application Priority Data

Sep. 13, 1996 [CH] Switzerland ............................ 2253/96

[51] Int. Cl.$^7$ .............................. C08K 5/34; C09K 15/22
[52] U.S. Cl. ........................................... 524/100; 252/403
[58] Field of Search ............................ 524/100; 252/403

[56] References Cited

U.S. PATENT DOCUMENTS

| | | | |
|---|---|---|---|
| 3,118,887 | 1/1964 | Hardy et al. ............................ | 260/248 |
| 3,242,175 | 3/1966 | Duennenberger et al. ............. | 260/248 |
| 3,244,708 | 4/1966 | Duennenberger et al. ............. | 260/248 |
| 3,249,608 | 5/1966 | Biland et al. ........................... | 260/248 |
| 3,444,164 | 5/1969 | Luethi et al. ........................... | 260/248 |
| 4,619,956 | 10/1986 | Susi ......................................... | 524/87 |
| 5,106,891 | 4/1992 | Valet ........................................ | 524/91 |
| 5,461,151 | 10/1995 | Waterman ............................... | 544/216 |

FOREIGN PATENT DOCUMENTS

| | | |
|---|---|---|
| 0165608 | 12/1985 | European Pat. Off. . |
| 0434608 | 6/1991 | European Pat. Off. . |
| 0444323 | 9/1991 | European Pat. Off. . |
| 0704437 | 4/1996 | European Pat. Off. . |
| 1321561 | 6/1973 | United Kingdom . |

*Primary Examiner*—Kriellion Sanders
*Attorney, Agent, or Firm*—Luther A. R. Hall

[57] ABSTRACT

Mixtures comprising a compound of the formula I and a compound of the formula II

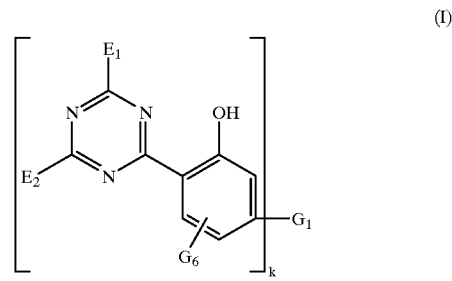

(I)

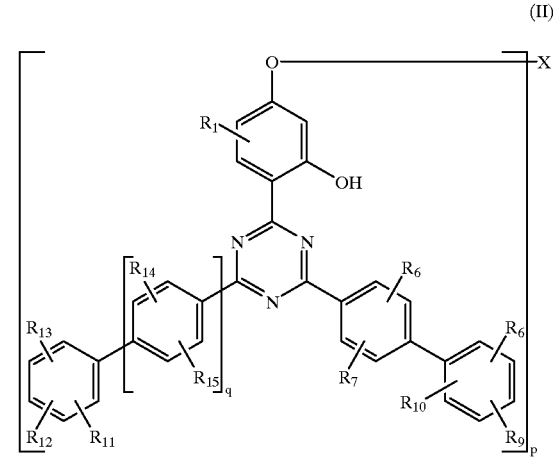

(II)

in which $E_1$ and $E_2$

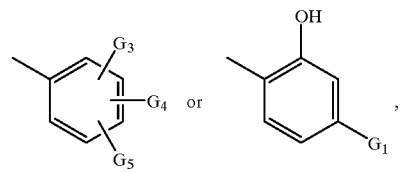

q is 0 or 1, p and k are each 1 or 2, and the remaining symbols are as defined in claim 1, are outstandingly suitable for stabilizing organic material, especially coating materials.

15 Claims, No Drawings

STABILIZER COMBINATION

The invention relates to a novel stabilizer mixture comprising compounds of the 2,4,6-triphenyl-1,3,5-triazine and 2-(4-phenylphenyl)-4,6-diaryl-1,3,5-triazine type, to organic material stabilized with the aid of this mixture against damage by light, heat and oxygen, and to the corresponding use of the mixtures as stabilizers for organic material.

If it is desired to increase the photostability of an organic material, especially a coating, it is common to add a light stabilizer. One very frequently employed class of light stabilizers are the UV absorbers, which protect the material by absorbing the damaging radiation by way of chromophores. One important group of UV absorbers is the triphenyltriazines, as are described, inter alia, in the publications U.S. Pat. No. 3,118,887, U.S. Pat. No. 3,242,175, U.S. Pat. No. 3,244,708, U.S. Pat. No. 3,249,608, GB-A-1,321,561, EP-A-434,608, U.S. Pat. 4,619,956, U.S. Pat. 5,461,151, EP-A-704,437. In addition, individual compounds of the 2-(4-phenylphenyl)-4,6-diaryl-1,3,5-triazine type have already been described (U.S. Pat. No. 3,242,175, U.S. Pat. No. 3,244,708, GB-A-1,321,561, U.S. Pat. 3,444,164, GB-A-2,286,774, GB-A-2,297,091, WO-96-28 431).

Furthermore, stabilizer mixtures comprising UV absorbers of the triphenyltriazine and o-hydroxyphenylbenzotriazole type (U.S. Pat. 5,106,891) and mono- and bisresorcinyltriazines (GB-A-2,297,091) have already been proposed.

Specific mixtures of compounds from the class of trisaryltriazines have now been found which, surprisingly, have particularly good stabilizer properties.

The invention therefore provides a mixture comprising a compound of the formula I

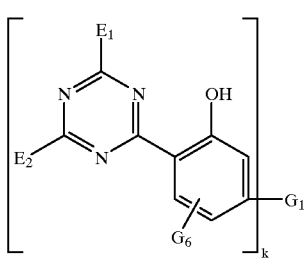

(I)

and a compound of the formula II

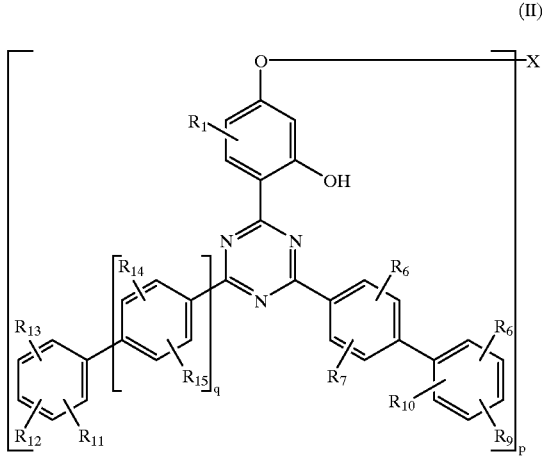

(II)

in which, in formula I
$G_1$ is hydrogen or —OG;
k is 1 or 2 ;and, if k=1,
$E_1$ and $E_2$, independently of one another, are a group of the formula Ia or Ib

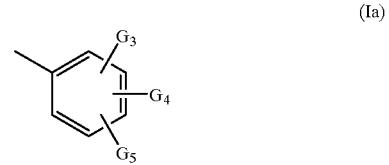

(Ia)

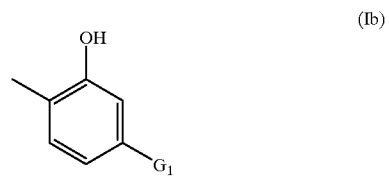

(Ib)

and G is hydrogen or $C_1$–$C_{18}$alkyl; or is $C_1$–$C_{18}$alkyl which is substituted by OH, $C_1$–$C_{18}$alkoxy, $C_5$–$C_{12}$cycloalkoxy, allyloxy, halogen, =O, —COOH, —COO$G_8$, —CONH$_2$, —CONH$G_9$, —CON($G_9$)($G_{10}$), —NH$_2$, —NH$G_9$, =N$G_9$, —N($G_9$)($G_{10}$), —NHCO$G_{11}$, —CN, —OCO$G_{11}$, phenoxy and/or $C_1$–$C_{18}$alkyl—, $C_1$–$C_{18}$alkoxy- or halo-substituted phenoxy; or G is $C_3$–$C_{50}$alkyl which is interrupted by —O— and can be substiituted by OH; or G is $C_3$–$C_6$alkenyl; glycidyl; $C_5$–$C_{12}$cycloalkyl; $C_5$–$C_{12}$cycloalkyl substituted by OH, $C_1$–$C_4$alkyl or —OCO$G_{11}$,; $C_7$–$C_{11}$phenylalkylwhich is unsubstituted or substituted by OH, Cl, $C_1$–$C_{18}$alkoxy or $C_1$–$C_{18}$alkyl; —CO—$G_{12}$ or —SO$_2$—$G_{13}$;

$G_3$, $G_4$ and $G_5$, independently of one another, are H; $C_1$–$C_{12}$alkyl; $C_2$–$C_6$alkenyl; $C_1$–$C_{18}$alkoxy; $C_5$–$C_{12}$cycloalkoxy; $C_2$–$C_{18}$alkenoxy; halogen; —C≡N; $C_1$–$C_4$haloalkyl; $C_7$–$C_{11}$phenylalkyl; $COOG_8$; $CONH_2$; $CONHG_9$; $CONG_9G_{10}$; sulfo; $C_2$–$C_{18}$acylamino; $OCOG_{11}$; phenyloxy; or phenyloxy, $C_1$–$C_{12}$alkyl or $C_1$–$C_{18}$alkoxy which is substituted by $C_1$–$C_{18}$alkyl, $C_1$–$C_{18}$alkoxy or halogen; and one radical $G_3$ in formula I additionally embraces the meaning —$NG_{16}G_{17}$; $G_6$ embraces the meanings set out below for R in formula II; $G_8$ is $C_1$–$C_{18}$alkyl; $C_3$–$C_{18}$alkenyl; $C_3$–$C_{50}$alkyl which is interrupted by O, NH, $NG_9$ or S and/or is substituted by OH; $C_1$–$C_4$alkyl which is substituted by —$P(O)(OG_{14})_2$, —$N(G_9)(G_{10})$ or —$OCOG_{11}$ and/or OH; glycidyl; $C_5$–$C_{12}$cycloalkyl; $C_1$–$C_4$alkylcyclohexyl; phenyl; $C_7$–$C_{14}$alkylphenyl; $C_6$–$C_{15}$bicycloalkyl; $C_6$–$C_{15}$bicycloalkenyl; $C_6$–$C_{15}$tricycloalkyl; $C_6$–$C_{15}$bicycloalkylalkyl; or $C_7$–$C_{11}$phenylalkyl; $G_9$ and $G_{10}$ independently of one another are $C_1$–$C_{12}$alkyl; $C_3$–$C_{12}$alkoxyalkyl; $C_2$–$C_{18}$alkanoyl; $C_4$–$C_{16}$dialkylaminoalkyl or $C_5$–$C_{12}$cycloalkyl; or $G_9$ and $G_{10}$ together are $C_3$–$C_9$alkylene or -oxaalkylene or -azaalkylene; $G_{11}$ is $C_1$–$C_{18}$alkyl; $C_1$–$C_{12}$alkoxy; $C_2$–$C_{18}$alkenyl; $C_7$–$C_{11}$phenylalkyl; $C_7$–$C_{11}$phenylalkoxy; $C_6$–$C_{12}$cycloalkyl; $C_6$–$C_{12}$cycloalkoxy; phenoxy or phenyl; or is $C_3$–$C_{50}$alkyl which is interrupted by —O—and can be substituted by OH;

$G_{12}$ is $C_1$–$C_{18}$alkenyl; $C_2$–$C_{18}$alkenyl; phenyl; $C_1$–$C_{18}$alkoxy; $C_3$–$C_{18}$alkenyloxy; $C_3$–$C_{50}$alkoxy which is interrupted by O, NH, $NG_9$ or S and/or is substituted by OH; cyclohexyloxy; phenoxy; $C_7$–$C_{14}$alkylphenoxy; $C_7$–$C_{11}$phenylalkoxy; $C_1$–$C_{12}$alkylamino; phenylamino; tolylamino or naphthylamino; $G_{13}$ is $C_1$–$C_{12}$alkyl; phenyl; naphthyl or $C_7$–$C_{14}$alkylphenyl; $G_{14}$ is $C_1$–$C_{12}$alkyl, methylphenyl or phenyl; $G_{16}$ is hydrogen or $C_1$–$C_{20}$alkyl; $G_{17}$ is hydrogen, $C_1$–$C_{20}$alkyl, $C_7$–$C_{13}$phenylalkyl, —C(=O)—$G_{19}$, —C(=O)—NH—$G_{16}$; and $G_{19}$ is $C_1$–$C_{20}$alkyl; $C_2$–$C_{20}$alkyl which is interrupted by 1 to 6 oxygen atoms and/or is substituted by OH, halogen, $NH_2$, $NHG_9$ or $NG_9G_{10}$ $C_1$–$C_{20}$alkoxy; phenyl; $C_7$–$C_{13}$phenylalkyl or $C_2$–$C_{20}$alkenyl;

and, if k=2, $E_1$ and $E_2$ are a group of the formula Ia; G is $C_2$–$C_{16}$alkylene, $C_4$–$C_{12}$alkenylene, xylylene, $C_3$–$C_{20}$alkylene which is interrupted by O and/or substituted by OH, or a group of the formula —$CH_2CH(OH)CH_2O$—$G_{20}$—$OCH_2CH(OH)CH_2$—, —CO—$G_{21}$—CO—, —CO—NH—$G_{22}$—NH—CO—, —$(CH_2)_j$—COO—$G_{20}$—OOC—$(CH_2)_j$—, in which j is a number from the range from 1 to 3, or is

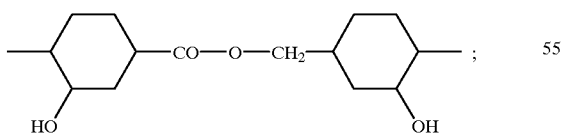

$G_{20}$ is $C_2$–$C_{10}$alkylene; $C_4$–$C_{50}$alkylene which is interrupted by O, phenylene, or a group -phenylene-E-phenylene-, in which E is —O—, —S—, —$SO_2$—, —$CH_2$—, —CO—, or —$C(CH_3)_2$—; $G_{21}$ is $C_2$–$C_{10}$alkylene, $C_2$–$C_{10}$oxaalkylene, $C_2$–$C_{10}$thiaalkylene, $C_6$–$C_{12}$arylene or $C_2$–$C_6$alkenylene; $G_{22}$ is $C_2$–$C_{10}$alkylene, phenylene, tolylene, diphenylenemethane or a group of the formula

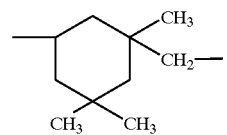

and the remaining radicals embrace the meanings indicated if k=1;

and in which, in formula II, $R_1$ is hydrogen; $C_1$–$C_{24}$alkyl or $C_5$–$C_{12}$cycloalkyl; or is $C_1$–$C_{24}$alkyl or $C_5$–$C_{12}$cycloalkyl which is substituted by 1 to 9 halogen atoms, —$R_4$, —$OR_5$, —$N(R_5)_2$, =$NR_5$, =O, —$CON(R_5)_2$, —$COR_5$, —$COOR_5$, —$OCOR_5$, —$OCON(R_5)_2$, —CN, —$NO_2$, —$SR_5$,—$SOR_5$, —$SO_2R_5$, —$P(O)(OR_5)_2$, a morpholinyl, piperidinyl, 2,2,6,6-tetramethylpipenidinyl, piperazinyl or N-methylpiperazinyl group or by combinations thereof; or is $C_5$–$C_{12}$cycloalkyl or $C_1$–$C_{24}$alkyl which is interrupted by 1 to 6 phenylene, —O—, —$NR_5$—, —$CONR_5$—, —COO—, —OCO—, —$CH(R_5)$—, —$C(R_5)_2$—or —CO—groups or combinations thereof; or $R_1$ is $C_2$–$C_{24}$alkenyl; halogen; —$SR_3$, $SOR_3$; $SO_2R_3$; —$SO_3H$; or $SO_3M$;

$R_3$ is $C_1$–$C_{20}$alkyl; $C_3$–$C_{18}$alkenyl; $C_5$–$C_{12}$cycloalkyl; $C_7$–$C_{15}$phenylalkyl, or $C_6$–$C_{12}$aryl which is unsubstituted or substituted by from 1 to 3 $C_1$–$C_4$alkyls;

$R_4$ is unsubstituted $C_6$–$C_{12}$aryl; or is $C_6$–$C_{12}$aryl substituted by 1 to 3 halogen atoms, $C_1$–$C_8$alkyl or $C_1$–$C_8$alkoxy or combinations thereof; $C_5$–$C_{12}$cycloalkyl; unsubstituted $C_7$–$C_{15}$-phenylalkyl; or is $C_7$–$C_{15}$phenylalkyl which is substituted in the phenyl ring by 1 to 3 halogen atoms, $C_1$–$C_8$alkyl, $C_1$–$C_8$alkoxy or combinations thereof; or is $C_2$–$C_8$alkenyl;

$R_5$ is $R_4$; hydrogen; $C_1$–$C_{24}$alkyl; or a radical of the formula

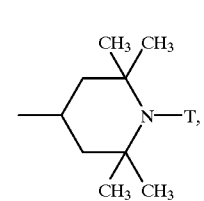

(Ia)

in which

T is hydrogen; $C_1$–$C_8$alkyl; $C_2$–$C_8$alkyl which is substituted by one or more hydroxyl groups or by one or more acyloxy groups; oxyl; hydroxyl; —$CH_2CN$; $C_1$–$C_{18}$alkoxy; $C_5$–$C_{12}$cycloalkoxy; $C_3$–$C_6$alkenyl; $C_7$–$C_9$phenylalkyl; $C_7$–$C_9$phenylalkyl which is substituted once, twice or three times in the phenyl ring by $C_1$–$C_4$alkyl; or is aliphatic $C_1$–$C_8$alkanoyl;

$R_6$ to $R_{15}$, independently of one another, are hydrogen; hydroxyl; —C≡N; $C_1$–$C_{20}$alkyl; $C_1$–$C_{20}$alkoxy; $C_7$–$C_{20}$phenylalkyl; $C_4$–$C_{12}$cycloalkyl; $C_4$–$C_{12}$cycloalkoxy; halogen; halo-$C_1$–$C_5$alkyl; sulfonyl; carboxyl; acylamino; acyloxy; $C_1$–$C_{12}$alkoxycarbonyl; aminocarbonyl; —O—Y; or —O—Z; or $R_8$ and $R_9$, together with the phenyl radical, are a cyclic radical which is interrupted by one or more oxygen or nitrogen atoms; and $R_{11}$, if q is 0, additionally comprises the meaning —$NG_{16}G_{17}$, where $G_{16}$ and $G_{17}$ have the meanings defined above;

M is alkali metal;
p is 1 or 2;
q is 0 or 1;
and if p=1,

X, Y and Z, independently of one another, are $R_y$; $C_1$–$C_{24}$alkyl substituted by $R_x$, $C_2$–$C_{50}$alkyl which is interrupted by one or more oxygen atoms and is substituted by one or more of the groups OH and/or $R_x$; $C_4$–$C_{12}$cycloalkyl substituted by $R_x$; $C_4$–$C_{12}$cycloalkyl substituted by —$OR_y$; $C_4$–$C_{20}$alkenyl interrupted by one or more oxygen atoms; or a radical of one of the formulae —CH((CH$_2$)$_n$—R$_2$)—CO—O—(CH$_2$)$_m$—R'$_2$; —CH((CH$_2$)$_n$—R$_2$)—CO—(NR')—(CH$_2$)$_m$—R'$_2$;

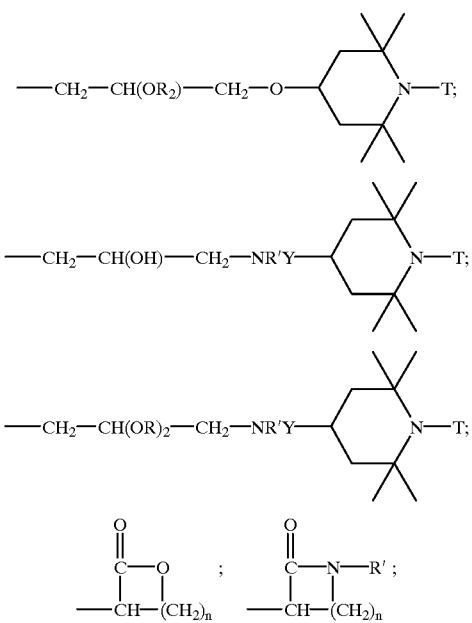

—CO—(CH$_2$)$_n$—R$_2$; —CO—O—(CH$_2$)$_n$—R$_2$; —CH$_2$—CH(—O—(CO)—R$_2$)—R'$_2$; —CO—N R'—(CH$_2$)$_n$—R$_2$;

R$_2$ and R'$_2$, independently of one another, if attached to a carbon atom, are $R_x$; and if attached to an atom other than carbon, are $R_y$;

n is 0 to 20; and
m is 0 to 20; and if p=2,

Y and Z, independently of one another, have the same meaning as for p=1; and

X is $C_2$–$C_{12}$alkylene; —CO—($C_2$–$C_{12}$alkylene)—CO—; —CO-phenylene-CO—; CO-biphenylene-CO—; CO—O—($C_2$–$C_{12}$alkylene)—O—CO—; —CO—O-phenylene-O—CO—; —CO—O-biphenylene-O—CO—; —CO—NR'—($C_2$–$C_{12}$alkylene)-NR'—CO—; —CO—NR'-phenylene-NR'—CO—; —CO—NR'-biphenylene-NR'—CO—; —CH$_2$—CH(OH)—CH$_2$—; —CH$_2$—CH(OR$_2$)—CH$_2$—; —CH$_2$—CH(OH)—CH$_2$—O—D—O—CH$_2$—CH(OH)—CH$_2$; —CH((CH$_2$)$_n$R$_2$)—COO—D—OOC—CH((CH$_2$)$_n$R$_2$)—; —CH$_2$—CH(OR$_2$)—CH$_2$—O—D—O—CH$_2$—CH(OR$_2$)—CH$_2$—;

D is $C_2$–$C_{12}$alkylene; $C_4$–$C_{50}$alkylene which is interrupted by one or more oxygen atoms; phenylene; biphenylene or phenylene-E-phenylene;

E is —O—; —S—; —SO$_2$—; —CH$_2$—; —CO—; or —C(CH$_3$)$_2$—;

$R_x$ is hydrogen; hydroxyl; $C_1$–$C_{20}$alkyl; $C_4$–$C_{12}$cycloalkyl; $C_1$–$C_{20}$alkoxy; $C_4$–$C_{12}$cycloalkoxy; $C_4$–$C_{12}$cycloalkyl or $C_4$–$C_{12}$cycloalkyloxy which is interrupted by one or more oxygen atoms; $C_6$–$C_{12}$aryl; hetero-$C_3$–$C_{12}$aryl; —$OR_z$; $NHR_z$; $R_z$; CONR'R"; allyl; $C_2$–$C_{20}$alkenyl; $C_4$–$C_{12}$cycloalkenyl; $C_4$–$C_{12}$cycloalkenyl which is interrupted by one or more oxygen atoms; $C_3$–$C_{20}$alkynyl; or $C_6$–$C_{12}$cycloalkynyl; or $C_1$–$C_{20}$alkyl, $C_2$–$C_{20}$alkoxy or $C_4$–$C_{12}$cycloalkyl each of which is substituted by hydroxyl, —NH$_2$, —NH—$C_1$–$C_8$alkyl, —NH-cyclohexyl, —N($C_1$–$C_8$alkyl)$_2$, dicyclohexylamino, halogen, $C_1$–$C_{20}$akyl, $C_1$–$C_{20}$alkoxy, $C_4$–$C_{12}$cycloalkyl, $C_4$–$C_{12}$cycloalkoxy, $C_2$–$C_{20}$alkenyl, $C_4$–$C_{12}$cycloalkyl, $C_3$–$C_{20}$alkynyl, $C_6$–$C_{12}$cycloalkynyl, $C_6$–$C_{12}$aryl, acylamine, acyloxy, sulfonyl, carboxyl, (meth)acryloxy, (meth)acrylamino,

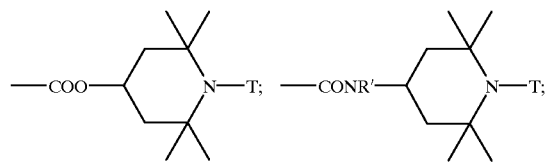

$R_y$ is hydrogen; $C_1$–$C_{20}$alkyl; $C_4$–$C_{12}$cycloalkyl; $C_4$–$C_{12}$cycloalkyl which is interrupted by one or more oxygen atoms; $C_6$–$C_{12}$aryl; hetero-$C_3$–$C_{12}$aryl; $R_z$; allyl; $C_2$–$C_{20}$alkenyl; $C_4$–$C_{12}$cycloalkenyl which is uninterrupted or is interrupted by one or more oxygen atoms; $C_3$–$C_{20}$akynyl; or $C_6$–$C_{12}$cycloalkynyl; or $C_1$–$C_{20}$alkyl or $C_4$–$C_{12}$cycloalkyl each of which is substituted by hydroxyl, —NH$_2$, —NH—$C_1$–$C_8$alkyl, —NH-cyclohexyl, —N($C_1$–$C_8$alkyl)$_2$, dicyclohexylamino, halogen, $C_1$–$C_{20}$alkyl, $C_1$–$C_{20}$alkoxy, $C_4$–$C_{12}$cycloalkyl, $C_4$–$C_{12}$cycloalkoxy, $C_2$–$C_{20}$alkenyl, $C_4$–$C_{12}$cycloalkyl, $C_3$–$C_{20}$alkynyl, $C_6$–$C_{12}$cycloalkynyl, $C_6$–$C_{12}$aryl, acylamine, acyloxy, sulfonyl, carboxyl, (meth)acryloxy, (meth)acrylamino,

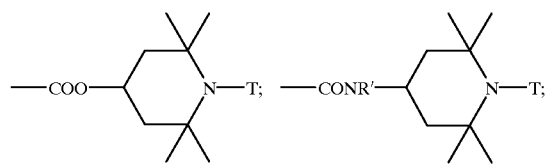

$R_z$ is —COR'; —COOR'; —CONR'R"; —CO—CH=CH$_2$; —CO—C(CH$_3$)=CH$_2$; R' and R", independently of one another, are hydrogen; $C_1$–$C_{20}$alkyl; $C_4$–$C_{50}$alkyl which is interrupted by one or more oxygen atoms; $C_4$–$C_{12}$cycloalkyl; $C_4$–$C_{12}$cycloalkyl which is interrupted by one or more oxygen atoms; $C_2$–$C_{20}$alkenyl; $C_2$–$C_{20}$alkenyl which is interrupted by one or more oxygen atoms; or are $C_6$–$C_{12}$aryl; or are $C_1$–$C_{20}$alkyl or $C_4$–$C_{12}$cycloalkyl each of which substituted by hydroxyl, —NH$_2$, —NH—$C_1$–$C_8$alkyl, —NH-cyclohexyl, —N($C_1$–$C_8$alkyl)$_2$, dicyclohexylamino, halogen, $C_1$–$C_{20}$alkyl, $C_1$–$C_{20}$alkoxy, $C_4$–$C_{12}$cycloalkyl, $C_4$–$C_{12}$cycloalkoxy, $C_2$–$C_{20}$alkenyl, $C_4$–$C_{12}$cycloalkyl, $C_3$–$C_{20}$alkynyl, $C_6$–$C_{12}$cycloalkynyl, $C_5$–$C_{12}$aryl, acylamine, acyloxy, sulfonyl, carboxyl, (meth)acryloxy, (meth)acrylamino,

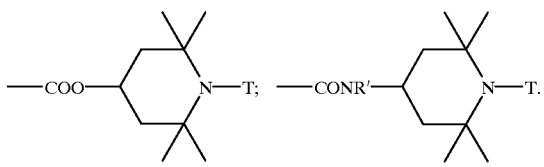

Mixtures which are of particular industrial interest are those of compounds of the formulae I and II whose hydroxyl groups para to the triazine ring are etherified or esterified, i.e. whose radicals G and X are not hydrogen.

Two or more radicals bearing the same designation can have identical or different meanings. For example, compounds of the formula I can include two or more groups of the formula Ia in which the radicals G can be identical or different.

$R_x$ bonds in each case to a carbon, $R_y$ to a heteroatom such as 0 or N, for example, especially O.

In preferred compounds of the formula II in the context of the invention:

$R_x$ is hydrogen; hydroxyl; $C_1$–$C_{20}$alkyl; $C_4$–$C_{12}$cycloalkyl; $C_1$–$C_{20}$alkoxy; $C_6$–$C_{12}$cycloalkoxy; phenyl; —$OR_z$; $NHR_z$; $R_z$; $CONR'R''$; allyl; or is $C_1$–$C_{20}$alkyl, $C_2$–$C_{20}$alkoxy or $C_4$–$C_{12}$cycloalkyl each of which is substituted by hydroxyl, $C_1$–$C_{20}$alkyl, $C_1$–$C_{20}$alkoxy, acyloxy, carboxyl, (meth)acryloxy; especially hydrogen; hydroxyl; $C_1$–$C_{12}$alkyl; $C_6$–$C_{12}$cycloalkyl; $C_1$–$C_{20}$alkoxy; $C_6$–$C_{12}$cycloalkoxy; phenyl; —$OR_z$; $R_z$; allyl; or $C_1$–$C_{20}$alkyl, $C_2$–$C_{20}$alkoxy or cyclohexyl, each of which is substituted by hydroxyl, $C_1$–$C_{12}$alkyl, $C_1$–$C_{12}$alkoxy, or carboxyl;

$R_y$ is hydrogen; $C_1$–$C_{20}$alkyl; $C_4$–$C_{12}$cycloalkyl; phenyl; $R_z$; allyl; or is $C_1$–$C_{20}$alkyl or $C_4$–$C_{12}$cycloalkyl each of which is substituted by hydroxyl, $C_1$–$C_{20}$alkyl, $C_1$–$C_{20}$alkoxy, acyloxy, carboxyl, (meth)acryloxy; especially hydrogen; $C_1$–$C_{12}$alkyl; $C_6$–$C_{12}$cycloalkyl; phenyl; $R_z$; allyl; or $C_1$–$C_{20}$alkyl or cyclohexyl each of which is substituted by hydroxyl, $C_1$–$C_{12}$alkyl, $C_1$–$C_{12}$alkoxy or carboxyl; and R' and R'', independently of one another, are hydrogen; $C_1$–$C_{20}$alkyl; $C_4$–$C_{12}$cycloalkyl; $C_2$–$C_3$alkenyl; phenyl; or are $C_1$–$C_{20}$alkyl or cyclohexyl each of which is substituted by hydroxyl, $C_1$–$C_{12}$alkyl, $C_1$–$C_{12}$alkoxy or carboxyl.

A substituent halogen is —F, —Cl, —Br or —I; preferably —F or —Cl, especially —Cl. $C_1$–$C_4$haloalkyl is alkyl substituted by one or more halogen atoms, for example chloromethyl, 2-chloroethyl, chloropropyl, chlorobutyl; of particular importance is trifluoromethyl.

An alkali metal is in general one of the metals Li, Na, K, Rb, Cs; in particular Li, Na, K; especially Na.

Alkylphenyl is phenyl substituted by alkyl; $C_7$–$C_{14}$alkylphenyl comprises, for example, methylphenyl (tolyl), dimethylphenyl (xylyl), trimethylphenyl (mesityl), ethylphenyl, propylphenyl, butylphenyl, dibutylphenyl, pentylphenyl, hexylphenyl, heptylphenyl, octylphenyl.

Phenylalkyl is alkyl substituted by phenyl; $C_7$–$C_{11}$, phenylalkyl comprises, for example, benzyl, α-methylbenzyl, α,α-dimethylbenzyl, phenylethyl, phenylpropyl, phenylbutyl, phenylpentyl.

Glycidyl is 2,3-epoxypropyl.

Alkyl interrupted by O, N or S and unsubstituted or substituted by OH can in general, within the context of the scope of meaning set out, contain one or more of the said heteroatoms, where oxygen, nitrogen and sulfur atoms do not occur adjacently. In general, a heteroatom in the alkyl chain and hydroxyl are not vicinal; preferably, a carbon atom of the alkyl chain bonds to not more than 1 oxygen, nitrogen and sulfur atom.

$C_1$–$C_{20}$alkoxy are straight-chain or branched radicals such as methoxy, ethoxy, propoxy, butoxy, pentyloxy, hexyloxy, heptyloxy, octyloxy, isooctyloxy, nonyloxy, undecyloxy, dodecyloxy, tetradecyloxy or pentadecyloxy, hexadecyloxy, heptadecyloxy, octadecyloxy, nonadecyloxy or eicosyloxy, for example.

Phenylalkyl is alkyl substituted by phenyl. $C_7$–$C_{20}$phenylalkyl comprises, for example, benzyl, α-methylbenzyl, α,α-dimethylbenzyl, phenylethyl, phenylpropyl, phenylbutyl, phenylpentyl, phenylhexyl, phenylheptyl, phenyloctyl, phenylnonyl, phenyldecyl, phenyldodecyl or phenyltetradecyl.

$C_4$–$C_{12}$cycloalkyl is, for example, cyclobutyl, cyclopentyl, cycloheptyl, cyclooctyl, cyclononyl, cyclodecyl, cycloundecyl, cyclododecyl and in particular, cyclohexyl.

Suitable examples of $C_4$–$C_{12}$cycloalkyl interrupted by one or more oxygen atoms are tetrahydrofuranyl, 1-oxa-4-cyclohexyl or 1,3-dioxa-4-cyclohexyl.

Within the context of the definitions indicated alkenyl comprises, inter alia, vinyl, allyl, isopropenyl, 2-butenyl, 3-butenyl, isobutenyl, n-penta-2,4-dienyl, 3-methyl-but-2-enyl, n-oct-2-enyl, n-dodec-2-enyl, iso-dodecenyl, n-dodec-2-enyl, n-octadec-enyl. $R_x$, R' and R'' as alkenyl are preferably $C_2$–$C_{18}$alkenyl, especially vinyl or allyl, $R_y$ is preferably $C_3$–$C_{18}$alkenyl, especially allyl.

$C_2$–$C_{18}$alkanoyl is, for example, acetyl, propionyl, acryloyl, methacryloyl or benzoyl.

$C_5$–$C_{12}$cycloalkenyl is, for example, 2-cyclopenten-1-yl, 2,4cyclopentadien-1-yl, 2-cyclohexen-1-yl, 2-cyclohepten-1-yl or 2-cycloocten-1-yl.

$C_4$–$C_{12}$cycloalkoxy is, for example, cyclobutyloxy, cyclopentyloxy, cyclohexyloxy, cycloheptyloxy, cyclooctyloxy, cyclononyloxy, cyclodecyloxy, cycloundecyloxy, cyclododecyloxy and, in particular, cyclohexyloxy.

Aryl is in general an aromatic hydrocarbon radical, for example phenyl, biphenylyl or naphthyl. Aralkyl is generally alkyl substituted by aryl; thus $C_7$–$C_{12}$aralkyl comprises, for example, benzyl, phenylethyl, phenylpropyl, phenylbutyl, phenylpentyl and phenyihexyl; benzyl and α-methylbenzyl are preferred. Alkylaryl is aryl substituted by abyl,; $C_7$–$C_{18}$alkylaryl comprises, inter alia, methylphenyl (tolyl), dimethylphenyl (xylyl), trimethylphenyl, tetramethylphenyl, pentamethylphenyl, ethylphenyl, propylphenyl (e.g.cumyl), butylphenyl (e.g. tert-butylphenyl), methylbutylphenyl, dibutylphenyl, pentylphenyl, hexylphenyl, dihexyiphenyl, heptylphenyl, octylphenyl, nonylphenyl, decylphenyl, undecylphenyl, dodecylphenyl, methylnaphthyl, dimethy Gnaphthyl, ethylnaphthyl, propyanaphthyl, butylnaphthyl, pentylnaphthyl, hexylnaphthyl, heptylnaphthyl, octylnaphthyl; of these, those of particular importance are, for example, tolyl, xylyl, propylphenyl and butylphenyl.

Particular examples of $C_6$–$C_{12}$aryl are phenyl, naphthyl and biphenylyl.

Hetero-$C_3$–$C_{12}$alyl is preferably pyridinyl, pyrimidinyl, terazinyl, pyrrolyl, furanyl, thiophenyl or quinolinyl.

The radicals G, $G_3$, $G_4$, $G_5$, $G_6$, $G_8$, $G_9$, $G_{10}$, $G_{11}$, $G_{12}$, $G_{13}$, $G_{14}$, $R_1$, $R_2$, $R'_2$, $R_3$, $R_5$, $R_6$ to $R_{15}$, $R_x$, $R_y$, T, X, Y, Z as alkyl are, in the context of the definitions indicated, branched or unbranched alkyl such as methyl, ethyl, propyl, isopropyl, n-butyl, sec-butyl, isobutyl, t-butyl, 2-ethylbutyl, n-pentyl, isopentyl, 1-methylpentyl, 1,3-di-methylbutyl, n-hexyl, 1-methylhexyl, n-heptyl, isoheptyl, 1,1,3,3-tetramethylbutyl, 1-methylheptyl, 3-methylheptyl, n-octyl, 2-ethyl hexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl. $G_3$, $G_4$, $G_5$, $R_6$ to $R_{15}$, $R'_2$, $R_2$, $G_8$, $G_9$, $G_{10}$, $G_{11}$, $G_{12}$, $G_{13}$, $G_{14}$ and T as alkyl are preferably short-chain, for example $C_1$–$C_8$alkyl, especially $C_1$–$C_4$alkyl such as methyl or butyl.

$G_3$, $G_4$, $G_5$ and $R_6$ to $R_{15}$ are independently of one another with particular preference hydrogen, methyl, methoxy, ethyl or isopropyl, especially hydrogen or methyl.

$G_9$ or $G_{10}$ as $C_4$–$C_{16}$dialkylaminoalkyl is alkyl, which is substituted by dialkylamino, the radical as a whole containing 4 to 16 carbon atoms. Examples thereof are $(CH_3)_2N$—$CH_2CH_2$—; $(C_2H_5)_2N$—$CH_2CH_2$—; $(C_3H_7)_2N$—$CH_2CH_2$—; $(C_4H_9)_2N$—$CH_2CH_2$—; $(C_5H_{11})_2N$—$CH_2CH_2$—; $(C_6H_{13})_2N$—$CH_2CH_2$—; $(CH_3)_2N$—$CH_2CH_2CH_2$—; $(C_2H_5)_2N$—$CH_2CH_2CH_2$—; $(C_3H_7)_2N$—$CH_2CH_2CH_2$—; $(C_4H_9)_2N$—$CH_2CH_2CH_2$—; $(C_5H_{11})_2N$—$CH_2CH_2CH_2$—; $(C_6H_{13})_2N$—$CH_2CH_2CH_2$—.

$G_9$ and $G_{10}$ in the conjoint meaning of $C_3$–$C_9$alkylene or -oxaalkylene or -azaalkylene are, together with the nitrogen atom to which they are attached, generally a 5- to 9-membered ring which contains 3 to 9 carbon atoms and may include further nitrogen or oxygen atoms, excluding directly adjacent nitrogen or oxygen atoms (structures of the hydrazine, oxylamine or peroxide type). Examples thereof include pyrrolidino, piperidino, piperazino, morpholino.

G or X, Y and/or Z as unsubstituted or substituted $C_5$–$C_{12}$cycloalkyl is, for example, cyclopentyl, cyclohexyl, cycloheptyl, cyclooctyl, cyclododecyl, methylcyclohexyl or acetyloxycyclohexyl; preference is given to cyclohexyl and cyclododecyl.

Where alkyl radicals carry further constituents or where individual radicals are alkylene, free valences and also bonds to substituents can start from the same carbon atom or from different carbon atoms. Preferably, bonds to heteroatoms start from different carbon atoms.

Thus G, X, Y and Z as substituted $C_1$–$C_{12}$alkyl comprise, for example, hydroxyalkyl, such as 2-hydroxyethyl, 3-hydroxypropyl or 2-hydroxypropyl; alkoxy-hydroxyalkyl, such as 2-hydroxy-3-methoxypropyl, 2-hydroxy-3-ethoxypropyl, 2-hydroxy-3-butoxypropyl, 2-hydroxy-3-hexoxypropyl or 2-hydroxy-3-(2-ethylhexyloxy)-propyl; alkoxycarbonylalkyl, such as methoxycarbonylmethyl, ethoxycarbonylmethyl, butoxycarbonylmethyl, octyloxycarbonylmethyl, 1-octyloxycarbonyl-1-methylmethyl, 1-octyloxycarbonyl-1-ethylmethyl or 1-octyloxycarbonyl-1-hexylmethyl; or alkanoyloxyalkyl or alkenoyloxyalkyl, such as 2-(acetyloxy)ethyl, 2-acryloxyethyl or 2-methacryloxyethyl; or, for example, 3-acryloxy- or 3-methacryloxy-2-hydroxypropyl.

G, X, Y and Z as alkyl which is substituted by OH, alkoxy, phenoxy, —$COOG_8$, and/or —$OCOG_{11}$ comprises, for example, the following meanings: —$CH_2CH(OH)CH_2O$—$R_{19}$, in which $R_{19}$ has one of the definitions indicated above for alkyl or can, for example, be phenyl, acetyl, propionyl, acryloyl or methacryloyl; or alkyloxycarbonylalkyl; examples of such radicals are —$CH_2CH_2OCOCH$=$CH_2$, —$CH_2CH(OH)C_8H_{17}$, —$CH_2CH(OH)C_{12}H_{25}$, —$CH_2CH(OH)CH_2O$—n—$C_8H_{17}$, —$CH_2CH(OH)CH_2O$—$C_6H_5$, —$CH_2CH(OH)CH_2O$—$CH_2CH(C_2H_5)$—$(CH_2)_3$—$CH_3$ —$OCH_2CH(OH)CH_2OCOC(CH_3)$=$CH_2$, —$OCH_2CH(OH)CH_2OCOCH$=$CH_2$.

G, X, Y and Z and also $G_8$ and $G_{11}$ as alkyl interrupted by O and unsubstituted or substituted by OH can be interrupted by one or more O and substituted by one or more OH. Preferably, these radicals are interrupted by two or more O, for example 2–12 oxygen atoms, and unsubstituted or substituted by 1–2 OH. $G_8$ or $G_{11}$ in this definition is preferably of the formula —$(CH_2CHG_{15}$—$O)_i$—$G_{18}$, and G, X, Y and Z are preferably of one of the formulae —$(CH_2CHG_{15}$—$O)_i$—$G_{18}$ or —$CH_2$—$CH(OH)$—$CH_2$—$O$—$(CH_2CHG_{15}$—$O)_i$—$G_{18}$, where i is a number from the range 1–16, in particular from the range 2–12, especially 4–10, $G_{15}$ is H or methyl and $G_{18}$ is H, $C_1$–$C_{18}$alkyl, phenyl or $C_7$–$C_{10}$alkylphenyl. A typical example of such radicals is polyoxyethylene, for example that having 4–10 ethyleneoxy units, which at the chain end carries a free hydroxyl group or is satisfied by alkyl.

Radicals referred to as acylamino or acyloxy, for example $R_6$ to $R_{15}$, are preferably $C_2$–$C_{12}$acylamino or -acyloxy, respectively.

Acyl is —CO—R, in which R is an organic radical containing in most cases 1–11 carbon atoms, generally $C_1$–$C_{11}$alkyl, $C_2$–$C_{11}$alkenyl, $C_6$–$C_{10}$aryl, $C_7$–$C_{11}$phenylalkyl or $C_7$–$C_{11}$alkylphenyl. In the context of the meaning indicated acylamino is frequently a radical —$N(R_2)$—CO—$R_2'$.

$R_6$ to $R_{15}$ independently of one another are preferably hydrogen; $C_1$–$C_{20}$ alkyl; $C_1$–$C_{20}$alkoxy; halogen. If q is 0, $R_{13}$ in the preferred meaning comprises additionally hydroxyl, and $R_{12}$ in the preferred meaning comprises additionally OY.

$R_1$ and $G_6$ independently of one another are preferably hydrogen, $C_1$–$C_{24}$alkyl, $C_5$–$C_{12}$cycloalkyl or $C_7$–$C_{15}$phenylalkyl, for example H, butyl, pentyl, hexyl, heptyl, octyl, cyclohexyl, benzyl, 1-phenylethyl or a radical of the formula

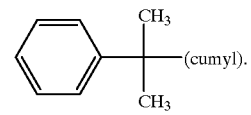

If not hydrogen, $R_1$ and $G_6$ are preferably in position 5 (para to OH and ortho to OG or OX). Compounds of particular importance are those in which $R_1$ and $G_6$ are hydrogen, $C_1$–$C_{10}$alkyl or $C_7$–$C_{15}$phenylalkyl. With particular preference $R_1$ and $G_6$ are each H.

Compounds of the formula II in the novel mixtures are, for example, those of the formulae

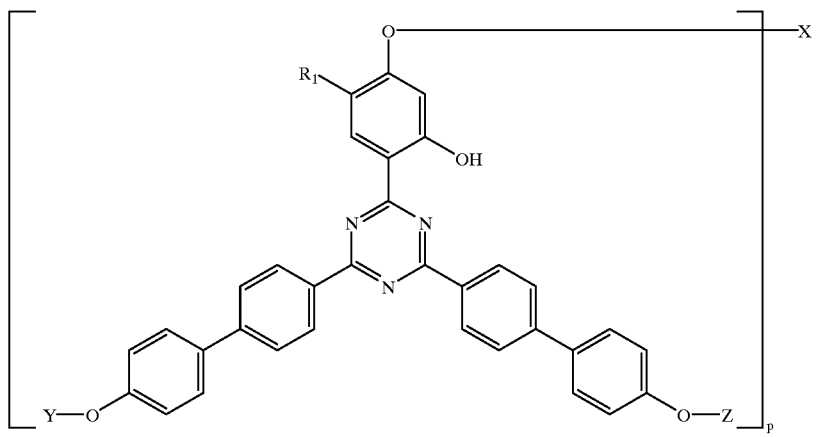

and in particular

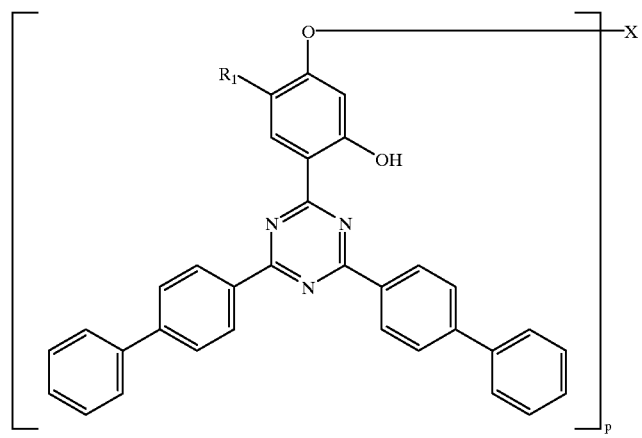

in which

R₁, X, Y, Z, and p have the meanings indicated for formula II.

If the novel mixture comprises a compound of the formula I in which G₆ is not hydrogen, then E₁ and E₂ are in most cases of the formula Ia.

If the novel mixture comprises a compound of the formula II in which R₁ is not hydrogen, then R₆–R₁₅ are in most cases hydrogen, C₁–C₂₀alkyl, C₁–C₂₀alkoxy or halogen.

Novel mixtures in which in the compounds of the formula I G₆ is H, and in the compounds of the formula II R₁ is not H and also those in which in the compounds of the formula I G₆ is not H, and in the compounds of the formula II R₁ is H, are in each case of special industrial interest.

If in the compound of the formula I in the novel mixture one of the radicals E₁ and E₂ is of the formula Ia and the other is of the formula Ib, then the compound of the formula II is preferably not one of the formulae

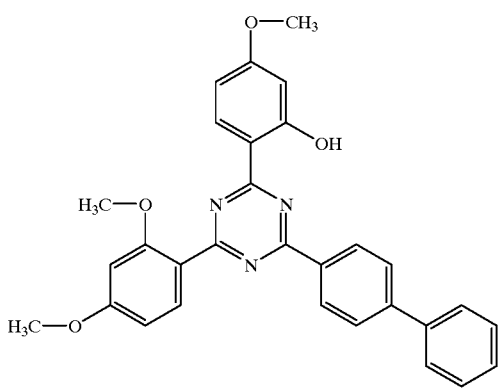

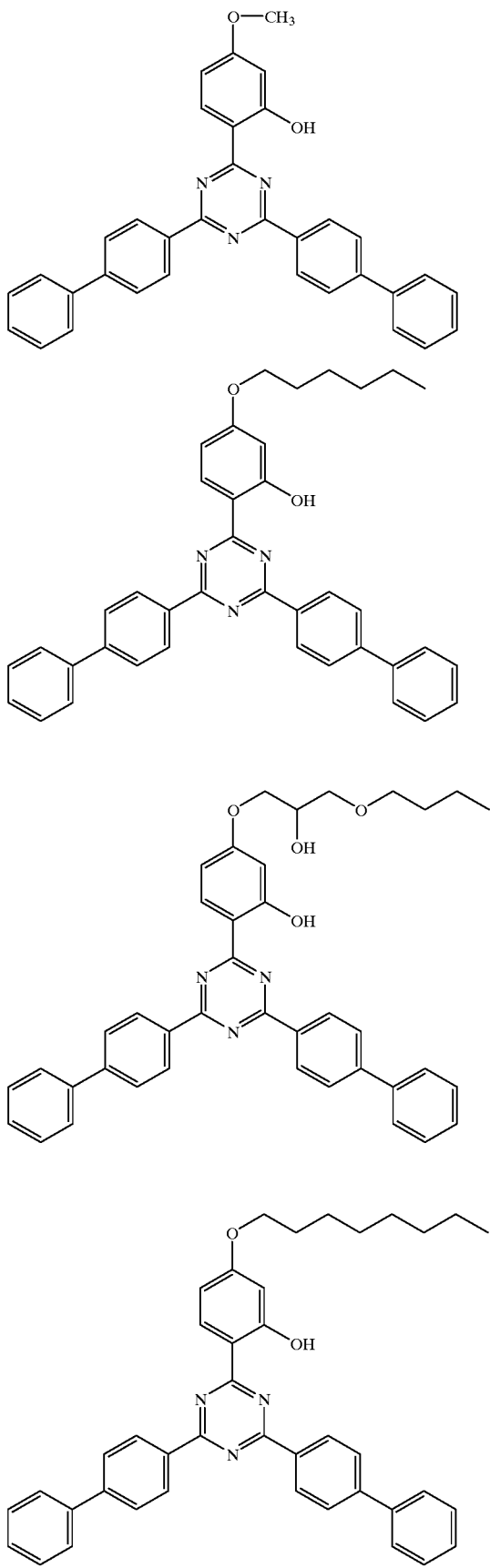

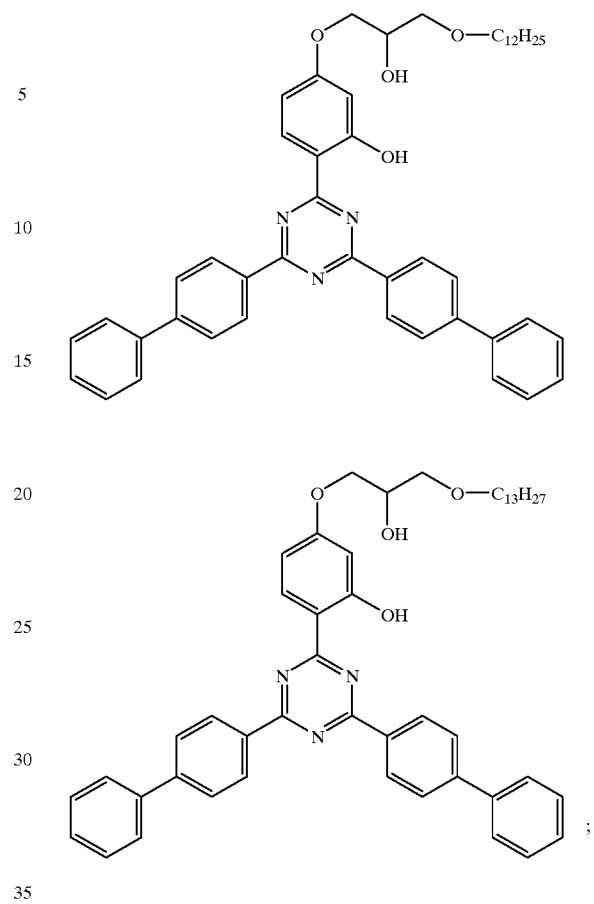

particular preference is given in this case to a compound of the formula II in which $R_1$ is not hydrogen and/or p is 2.

If in the compounds of the formula I in the novel mixture both radicals $E_1$ and $E_2$ are of the formula I*a*, then the compound of the formula II is preferably not of the formula

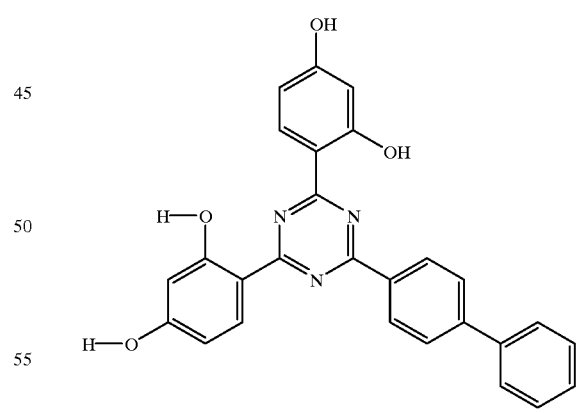

Particular preference is given in this case to a compound of the formula II in which $R_1$ is not hydrogen and/or in which X is not hydrogen and none of the radicals $R_{11}$ to $R_{13}$ is hydroxyl.

Of especial interest are novel mixtures in which in formula I both radicals $E_1$ and $E_2$ are either of the formula I*a* or of the formula I*b*, in particular both of the formula I*a*, and in which in the formula II none of the radicals $R_{11}$ to $R_{13}$ is hydroxyl, and those in which in formula I one of the radicals $E_1$ and $E_2$ is of the formula I$a$ and the other is of the formula I$b$, or both are of the formula I$b$ and in which, in the formula II, q is 0 and one of the radicals $R_{11}$ to $R_{13}$ is in position 2 relative to the triazine ring and is hydroxyl.

k is preferably 1.

Where compounds of the formula I include a radical of the formula I$a$, then the substituents $G_3$–$G_5$ therein are preferably in positions 2,4,6 relative to the triazine ring, in accordance with the formula

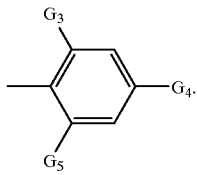

Of particular interest for use in the novel mixtures are those compounds of the formula I in which k is 1, $G_3$, $G_4$ and $G_5$, independently of one another, are hydrogen or methyl, $G_6$ is hydrogen and G is $C_1$–$C_{18}$alkyl or 3-($C_3$–$C_{18}$alkoxy)-2-hydroxypropyl. Where two or more radicals G are present, they are preferably identical.

Where $R_{11}$ and $R_{12}$ together with the phenyl radical form a cyclic radical, this radical is, for example, 3,4-dimethylenedioxyphenyl.

$R_x$ is frequently hydrogen; a radical substituted by $R_x$ is in this case an unsubstituted radical.

Of particular importance is a novel mixture comprising instead of the compound of the formula I a compound of the formula I'

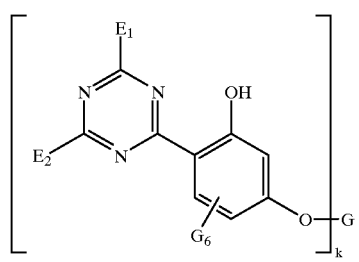

and in which in formula I'k is 1 or 2; and, if k=1, $E_1$ and $E_2$, independently of one another, are a group of the formula I$a$ or I'$b$

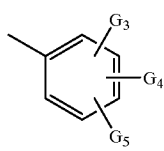

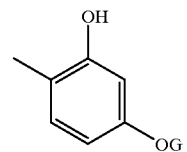

and
G is hydrogen or $C_1$–$C_{18}$alkyl; or is $C_1$–$C_{18}$alkyl which is substituted by OH, $C_1$–$C_{18}$-alkoxy, allyloxy, halogen, =O, —COOH, —COO$G_8$, —CON$H_2$, —CONH$G_9$, —CON($G_9$)($G_{10}$), —N$H_2$, —NH$G_9$, =N$G_9$, —N($G_9$)($G_{10}$), —NHCO$G_{11}$, —CN, —OCO$G_{11}$, phenoxy and/or $C_1$–$C_{18}$alkl-, $C_1$–$C_{18}$alkoxy- or halo-substituted phenoxy; or G is $C_3$–$C_{50}$alkyl which is interrupted by —O—and can be substituted by OH; or G is $C_3$–$C_6$alkenyl; glycidyl; $C_5$–$C_{12}$cycloalkyl; $C_5$–$C_{12}$cycloalkyl substituted by OH, $C_1$–$C_4$alkyl or —OCO$G_{11}$; $C_7$–$C_{11}$phenylalkl which is unsubstituted or substituted by OH, Cl, $C_1$–$C_{18}$alkoxy or $C_1$–$C_{18}$alkyl; —CO—$G_{12}$ or —$SO_2$—$G_{13}$; $G_3$, $G_4$ and $G_5$, independently of one another, are H, $C_1$–$C_{12}$alkyl; $C_2$–$C_6$alkenyl; $C_1$–$C_{18}$alkoxy; $C_5$–$C_{12}$cycloalkoxy; $C_2$–$C_{18}$alkenoxy; halogen; —C≡N; $C_1$–$C_4$haloalkyl; $C_7$–$C_{11}$phenylalkyl; COO$G_8$; CON$H_2$; CONH$G_9$; CON$G_9G_{10}$; sulfo; $C_2$–$C_{18}$acylamino; OCO$G_{11}$; phenyloxy; or phenyloxy, $C_1$–$C_{12}$alkyl or $C_1$–$C_{18}$alkoxy which is substituted by $C_1$–$C_{18}$alkyl, $C_1$–$C_{18}$alkoxy or halogen; $G_6$ embraces the meanings set out above for $R_1$ in formula II; $G_8$ is $C_1$–$C_{18}$alkyl; $C_2$–$C_{18}$alkenyl; $C_3$–$C_{50}$alkyl which is interrupted by O, NH, N$G_9$ or S and/or is substituted by OH; $C_1$–$C_4$alkyl which is substituted by —P(O)(O$G_{14}$)$_2$, —N($G_9$)($G_{10}$) or —OCO$G_{11}$ and/or OH; glycidyl; cyclohexyl; phenyl; $C_7$–$C_{14}$alkylphenyl or $C_7$–$C_{11}$phenylalkyl; $G_9$ and $G_{10}$ independently of one another, are $C_1$–$C_{12}$alkyl; $C_3$–$C_{12}$alkoxyalkyl; $C_2$–$C_{18}$alkanoyl; $C_4$–$C_{16}$dialkylaminoalkyl or $C_5$–$C_{12}$cycloalkyl; or $G_9$ and $G_{10}$ together are $C_3$–$C_9$alkylene or -oxaalkylene or -azaalkylene; $G_{11}$ is $C_1$–$C_{18}$alkyl; $C_2$–$C_{18}$alkenyl or phenyl; or is $C_3$–$C_{50}$alkyl which is interrupted by —O—and can be substituted by OH; $G_{12}$ is $C_1$–$C_{18}$alkyl; $C_2$–$C_{18}$alkenyl; phenyl; $C_1$–$C_{18}$alkoxy; $C_3$–$C_{18}$alkenyloxy; $C_3$–$C_{50}$alkoxy which is interrupted by O, NH, N$G_9$ or S and/or is substituted by OH; cyclohexyloxy; phenoxy; $C_7$–$C_{14}$alkylphenoxy; $C_{11}$–$C_{11}$phenylalkoxy; $C_1$–$C_{12}$alkylamino; phenylamino; tolylamino or naphthylamino; $G_{13}$ is $C_1$–$C_{12}$alkyl; phenyl; naphthyl or $C_7$–$C_{14}$alkylphenyl; $G_{14}$ is $C_1$–$C_{12}$alkyl, methylphenyl or phenyl; and, if k=2, $E_1$ and $E_2$ are a group of the formula I$a$; G is $C_2$–$C_{16}$alkylene, $C_4$–$C_{12}$alkenylene, xylylene, $C_3$–$C_{20}$alkylene which is interrupted by O and/or substituted by OH, or a group of one of the formulae —$CH_2$CH(OH)$CH_2$O—$G_{20}$—OC$H_2$CH(OH)$CH_2$—, —CO—$G_{21}$CO—, —CO—NH—$G_{22}$—NH—CO—, —($CH_2$)$_j$—COO—$G_{23}$—OOC—($CH_2$)$_j$—, in which j is a number from the range from 1 to 3,

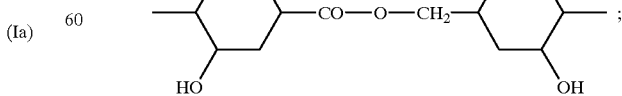

$G_{20}$ is $C_2$–$C_{10}$alkylene; $C_4$–$C_{50}$alkylene which is interrupted by O, phenylene, or a group -phenylene-E-phenylene-, in which E is —O—, —S—, —$SO_2$—, —$CH_2$—, —CO—, or —C(CH$_3$)$_2$—; G$_{21}$ is C$_2$–C$_{10}$alkylene, C$_2$–C$_{10}$oxaalkylene, C$_2$–C$_{10}$thiaalkylene, C$_6$–C$_{12}$arylene or C$_2$–C$_6$alkenylene; G$_{22}$ is C$_2$–C$_{10}$alkylene, phenylene, tolylene, diphenylenemethane or a group of the formula

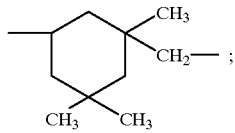

G$_{23}$ is C$_2$–C$_{10}$alkylene or C$_4$–C$_{20}$alkylene which is interrupted by O; and the remaining radicals embrace the meanings indicated for k=1;
and in which, in formula II, R$_1$ is hydrogen; C$_1$–C$_{24}$alkyl or C$_5$–C$_{12}$cycloalkyl; or is C$_1$–C$_{24}$alkyl or C$_5$–C$_{12}$cycloalkyl which is substituted by 1 to 9 halogen atoms, —R$_4$, —OR$_5$, —N(R$_5$)$_2$, =NR$_5$, =O, —CON(R$_5$)$_2$, —COR$_5$, —COOR$_5$, —OCOR$_5$, —OCON(R$_5$)$_2$, —CN, —NO$_2$, —SR$_5$,— SOR$_5$, —SO$_2$R$_5$, —P(O)(OR$_5$)$_2$, a morpholinyl, piperidinyl, 2,2,6,6-tetramethylpiperidinyl, piperazinyl- or N-methylpiperazinyl group or by combinations thereof; or is C$_5$–C$_{12}$cycloalkyl or C$_1$–C$_{24}$alkyl which is interrupted by 1 to 6 phenylene, —O—, —NR$_5$—, —CONR$_5$—, —COO—, —OCO—, —CH(R$_5$)—, —C(R$_5$)$_2$— or —CO— groups or combinations thereof; or R$_1$ is C$_2$–C$_{24}$alkenyl; halogen; —SR$_3$, SOR$_3$; SO$_2$R$_3$; —SO$_3$H; or SO$_3$M;

R$_3$ is C$_1$–C$_{20}$alkyl; C$_3$–C$_{18}$alkenyl; C$_5$–C$_{12}$cycloalkyl; C$_7$–C$_{15}$phenylalkyl, or C$_6$–C$_{12}$aryl which is unsubstituted or substituted by from 1 to 3 C$_1$–C$_4$alkyls;

R$_4$ is unsubstituted C$_6$–C$_{12}$aryl; or is C$_6$–C$_{12}$aryl substituted by 1 to 3 halogen atoms, C$_1$–C$_8$alkyl or C$_1$–C$_8$alkoxy or combinations thereof; C$_5$–C$_{12}$cycloalkyl; unsubstituted C$_7$–C$_{15}$phenylalkyl; or is C$_7$–C$_{15}$phenyl alkyl which is substituted in the phenyl ring by 1 to 3 halogen atoms, C$_1$–C$_8$alkyl, C$_1$–C$_8$alkoxy or combinations thereof; or is C$_2$–C$_8$alkenyl;

R$_5$ is R$_4$; hydrogen, C$_1$–C$_{24}$alkyl; or a radical of the formula

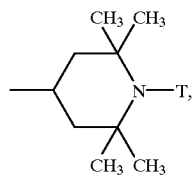

(1a)

in which

T is hydrogen; C$_1$–C$_8$alkyl; C$_2$–C$_8$alkyl which is substituted by one or more hydroxyl groups or by one or more acyloxy groups; oxyl; hydroxyl; —CH$_2$CN; C$_1$–C$_{18}$alkoxy; C$_5$–C$_{12}$cycloalkoxy; C$_3$–C$_6$alkenyl; C$_7$–C$_9$phenylalkyl; C$_7$–C$_9$phenylalkyl which is substituted once, twice or three times in the phenyl ring by C$_1$–C$_4$alkyl; or is aliphatic C$_1$–C$_8$alkanoyl;

R$_6$ to R$_{15}$, independently of one another, are hydrogen; hydroxyl; —C≡N; C$_1$–C$_{20}$alkyl; C$_1$–C$_{20}$alkoxy; C$_7$–C$_{20}$phenylalkyl; C$_4$–C$_{12}$cycloalkyl; C$_4$–C$_{12}$cycloalkoxy; halogen; halo-C$_1$–C$_5$alkyl; sulfonyl; carboxyl; acylamino; acyloxy; C$_1$–C$_{12}$alkoxycarbonyl; aminocarbonyl; —O—Y; or —O—Z; or R$_8$ and R$_9$, together with the phenyl radical, are a cyclic radical which is interrupted by one or more oxygen or nitrogen atoms;

M is alkali metal;
p is 1 or 2;
q is 0 or 1;
and if p=1,

X, Y and Z, independently of one another, are R$_y$; C$_1$–C$_{24}$alkyl substituted by R$_x$; C$_2$–C$_{50}$alkyl which is interrupted by one or more oxygen atoms and is substituted by one or more of the groups OH and/or R$_x$; C$_4$–C$_{12}$cycloalkyl substituted by R$_x$, C$_4$–C$_{12}$cycloalkyl substituted by —OR$_y$; C$_4$–C$_{20}$alkenyl interrupted by one or more oxygen atoms; or a radical of one of the formulae —CH((CH$_2$)$_n$—R$_2$)—CO—O—(CH$_2$)$_m$— R'$_2$; —CH((CH$_2$)$_n$—R$_2$)—CO—(NR')—(CH$_2$)$_m$—R'$_2$;

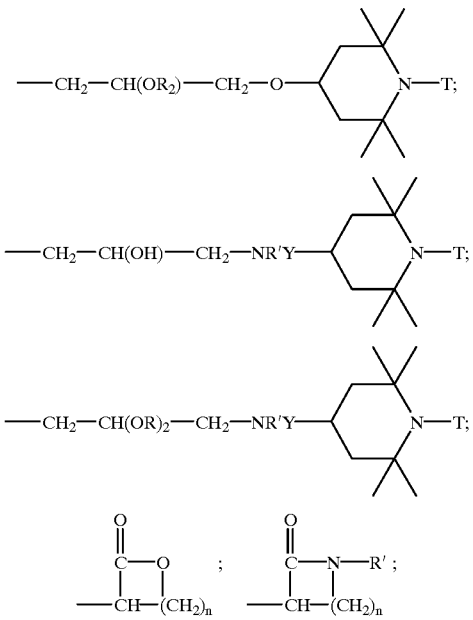

—CO—(CH$_2$)$_n$—R$_2$; —CO—O—(CH$_2$)$_n$—R$_2$; —CH$_2$—CH(—O—(CO)—R$_2$)—R'$_2$; —CO—NR'— (CH$_2$)$_n$—R$_2$;

R$_2$ and R'$_2$, independently of one another, if attached to a carbon atom, are R$_x$; and, if attached to an atom other than carbon, are R$_y$;

n is 0 to 20; and
m is 0 to 20; and,
if p=2,

Y and Z, independently of one another, have the same meaning as for p=1; and

X is C$_2$–C$_{12}$alkylene; —CO—(C$_2$–C$_{12}$alkylene)—CO—; —CO-phenylene-CO—; CO-biphenylene-CO—; CO—O—(C$_2$–C$_{12}$alkylene)—O—CO—; —CO—O-phenylene-O—CO—; —CO—O-biphenylene-O—CO—; —CO—NR'—(C$_2$–C$_{12}$alkylene)-NR'—CO—; —CO—NR'-phenylene-NR'—CO—; —CO—NR'-biphenylene-NR'—CO—; —CH$_2$—CH(OH) —CH$_2$—; —CH$_2$—CH(OR$_2$) —CH$_2$—; —CH$_2$—CH (OH)—CH$_2$—O—D—O—CH$_2$—CH(OH)—CH$_2$; —CH$_2$—CH(OR$_2$)—CH$_2$—O—D—O—CH$_2$—CH (OR$_2$)—CH$_2$—;

D is C$_2$–C$_{12}$alkylene; C$_4$–C$_{50}$alkylene which is interrupted by one or more oxygen atoms; phenylene; biphenylene or phenylene-E-phenylene;

E is —O—; —S—; —SO$_2$—; —CH$_2$—; —CO—; or —C(CH$_3$)$_2$—;

R$_x$ is hydrogen; hydroxyl; C$_1$–C$_{20}$alkyl; C$_4$–C$_{12}$cycloalkyl; C$_1$–C$_{20}$alkoxy; C$_4$–C$_{12}$cycloalkoxy; C$_4$–C$_{12}$cycloalkyl or C$_4$–C$_{12}$cycloalkyloxy which is interrupted by one or more oxygen atoms; C$_6$–C$_{12}$aryl; hetero-C$_3$–C$_{12}$aryl; —OR$_z$; NHR$_z$; R$_z$; CONR'R''; allyl; C$_2$–C$_{20}$alkenyl; C$_4$–C$_{12}$cycloalkenyl; C$_4$–C$_{12}$cycloalkenyl which is interrupted by one or more oxygen atoms; C$_3$–C$_{20}$alkynyl; or C$_6$–C$_{12}$cycloalkynyl;

R$_y$ is hydrogen; C$_1$–C$_{20}$alkyl; C$_4$–C$_{12}$cycloalkyl; C$_4$–C$_{12}$cycloalkyl which is interrupted by one or more oxygen atoms; C$_6$–C$_{12}$aryl; hetero-C$_3$–C$_{12}$aryl; R$_z$; allyl; C$_2$–C$_{20}$alkenyl; C$_4$–C$_{12}$cycloalkenyl which is uninterrupted or is interrupted by one or more oxygen atoms; C$_3$–C$_{20}$alkynyl; or C$_6$–C$_{12}$cycloalkynyl;

R$_z$ is —COR'; —COOR'; —CONR'R''; —CO—CH=CH$_2$; —CO—C(CH$_3$)=CH$_2$; R' and R'', independently of one another, are hydrogen; C$_1$–C$_{20}$alkyl; C$_4$–C$_{50}$alkyl which is interrupted by one or more oxygen atoms; C$_4$–C$_{12}$cycloalkyl; C$_4$–C$_{12}$cycloalkyl which is interrupted by one or more oxygen atoms; C$_2$–C$_{20}$alkenyl; C$_2$–C$_{20}$alkenyl which is interrupted by one or more oxygen atoms; or are C$_6$–C$_{12}$aryl.

The novel mixtures preferably contain from 0.2 to 5 parts by weight, for example from 0.2 to 1 part by weight and, in particular, from 0.3 to 3 parts by weight of a compound of the formula II per part by weight of a compound of the formula I.

Preference is likewise given to a mixture in which in the compound of the formula I G, if k=1, is hydrogen, C$_1$–C$_{18}$alkyl, allyl, glycidyl or benzyl; or is C$_1$–C$_{12}$alkyl which is substituted by OH, C$_1$–C$_{18}$alkoxy, C$_5$–C$_{12}$cycloalkoxy, phenoxy, —COOG$_8$, —CONHG$_9$, —CON(G$_9$)(G$_{10}$) and/or —OCOG$_{11}$; or G is —(CH$_2$CHG$_{15}$—O)$_i$—G$_{18}$ or —CH$_2$—CH(OH)—CH$_2$—O—(CH$_2$CHG$_{15}$—O)$_i$—G$_{18}$ where i is a number from the range 1–12;

G, if k=2, is C$_2$–C$_{16}$alkylene, C$_4$–C$_{12}$alkenylene, xylylene, or is C$_3$–C$_{20}$alkylene interrupted by O and/or substituted by OH; G$_3$, G$_4$ and G$_5$, independently of one another, are H, C$_1$–C$_{12}$alkyl, C$_2$–C$_6$alkenyl, C$_1$–C$_{12}$alkoxy, Cl, F; and a radical G$_3$ in formula I additionally comprises NG$_{16}$G$_{17}$; G$_6$ is hydrogen, C$_1$–C$_{24}$alkyl, C$_5$–C$_{12}$cycloalkyl or C$_7$–C$_{15}$phenylalkyl; G$_8$ is C$_1$–C$_{12}$alkyl; C$_3$–C$_{18}$alkenyl; C$_3$–C$_{20}$alkyl which is interrupted by O and/or substituted by OH; C$_5$–C$_{12}$cycloalkyl; C$_1$–C$_4$alkylcyclohexyl; or is C$_1$–C$_4$alkyl substituted by —P(O)(OG$_{14}$)$_2$; G$_9$ and G$_{10}$, independently of one another, are C$_1$–C$_8$alkyl or cyclohexyl; or G$_9$ and G$_{10}$ together are pentamethylene or 3-oxapentamethylene; G$_{11}$ is C$_1$–C$_8$alkyl, C$_2$–C$_5$alkenyl, cyclohexyl or phenyl; or is C$_3$–C$_{20}$alkyl which is interrupted by —O— and can be substituted by OH; and G$_{14}$ is C$_1$–C$_4$alkyl; G$_{15}$ is H or methyl; G$_{16}$ is hydrogen; G$_{17}$ is hydrogen, C$_1$–C$_{20}$alkyl, CO—G$_{19}$; G$_{18}$ is H, C$_1$–C$_{18}$alkyl, phenyl or C$_7$–C$_{10}$alkylphenyl; and G$_{19}$ is C$_1$–C$_{20}$alkyl; C$_2$–C$_{20}$alkenyl, C$_1$–C$_{20}$alkoxy or C$_2$–C$_{20}$alkyl which is interrupted by O; and in which in the compound of the formula II R$_1$ is hydrogen; C$_1$–C$_{24}$alkyl, C$_5$–C$_{12}$cycloalkyl or C$_7$–C$_{15}$phenylalkyl;

R$_6$ to R$_{15}$, independently of one another, are H, C$_1$–C$_{12}$alkyl, C$_2$–C$_6$alkenyl, Cl, F, OY or OZ;

p is 1; and q is 0 or 1;

X, Y and Z, independently of one another, are R$_y$; C$_1$–C$_{24}$alkyl which is substituted by R$_x$; C$_2$–C$_{50}$alkyl which is interrupted by one or more oxygen atoms and substituted by one or more of the groups OH and/or R$_x$; or are a radical of one of the formulae —CH((CH$_2$)$_n$—R$_2$)—CO—O—(CH$_2$)$_m$—R'$_2$; —CH((CH$_2$)$_n$—R$_2$)—CO—(NR')—(CH$_2$)$_m$—R'$_2$; —CO—(CH$_2$)$_n$—R$_2$; —CO—O—(CH$_2$)$_n$—R$_2$; —CH$_2$—CH(—O—(CO)—R$_2$)—R'$_2$; —CO—NR'—(CH$_2$)$_n$—R$_2$;

R$_2$ and R'$_2$, independently of one another, if attached to a carbon atom, are R$_x$; and, if attached to an atom other than carbon, are R$_y$;

n is 0 to 20; and m is 0 to 20; and

R$_x$ is hydrogen; hydroxyl; C$_1$–C$_{20}$alkyl; C$_4$–C$_{12}$cycloalkyl; C$_1$–C$_{20}$alkoxy; C$_6$–C$_{12}$cycloalkoxy; phenyl; —OR$_z$; NHR$_z$; R$_z$; allyl; or C$_1$–C$_{20}$alkyl, C$_2$–C$_{20}$alkoxy or C$_4$–C$_{12}$cycloalkyl, each of which is substituted by hydroxyl, C$_1$–C$_{20}$alkyl, C$_1$–C$_{20}$alkoxy, acyloxy, carboxyl, or (meth)acryloxy;

R$_y$ is hydrogen; C$_1$–C$_{20}$alkyl; C$_4$–C$_{12}$cycloalkyl; phenyl; R$_z$; allyl; or C$_1$–C$_{20}$alkyl or C$_4$–C$_{12}$cycloalkyl, each of which is substituted by hydroxyl, C$_1$–C$_{20}$alkyl, C$_1$–C$_{20}$alkoxy, acyloxy, carboxyl or (meth)acryloxy;

R$_z$ is —COR'; —COOR'; —CONR'R''; —CO—CH=CH$_2$; —CO—C(CH$_3$)=CH$_2$; R' and R'', independently of one another, are hydrogen; C$_1$–C$_{20}$alkyl; C$_4$–C$_{20}$alyl which is interrupted by oxygen; C$_4$–C$_{12}$cycloalkyl; C$_2$–C$_3$alkenyl; phenyl; or are C$_1$–C$_{20}$alkyl or cyclohexyl each of which is substituted by hydroxyl, C$_1$–C$_{12}$alkyl, C$_1$–C$_{12}$alkoxy or carboxyl.

Particular preference is given to a mixture in which in the compound of the formula I k is 1; G is hydrogen; C$_1$–C$_{18}$alkyl; C$_1$–C$_{12}$alkyl substituted by OH, C$_1$–C$_{18}$alkoxy, C$_5$–C$_{12}$cycloalkoxy, —COOG$_8$, —CON(G$_9$)(G$_{10}$), phenoxy and/or —OCOG$_{11}$, glycidyl or benzyl; or G is —(CH$_2$CHG$_{15}$—O)$_i$—G$_{18}$ or —CH$_2$—CH(OH)—CH$_2$—O—(CH$_2$CHG$_{15—O})_i$—G$_{18}$, where i is a number in the range 2–12; G$_8$ is C$_1$–C$_{12}$alkyl; C$_3$–C$_{12}$alkenyl; C$_6$–C$_{20}$alkyl which is interrupted by O and/or substituted by OH; C$_5$–C$_{12}$cycloalkyl; C$_1$–C$_4$alkylcyclohexyl; or C$_1$–C$_4$alkyl which is substituted by —P(O)(OG$_{14}$)$_2$; G$_9$ and G$_{10}$ are C$_4$–C$_8$alkyl; G$_{11}$ is C$_1$–C$_8$alkyl, cyclohexyl or C$_2$–C$_3$alkenyl; or is C$_3$–C$_{20}$alkyl which is interrupted by —O— and can be substituted by OH; G$_{14}$ is C$_1$–C$_4$alkyl; G$_{15}$ is hydrogen; and G$_{18}$ is H, C$_1$–C$_{18}$alkyl, phenyl or C$_7$–C$_{10}$alkylphenyl; and in which in the compound of the formula II R$_6$ to R$_{15}$, independently of one another, are H, C$_1$–C$_{12}$alkyl, Cl and R$_{11}$, R$_{12}$ and R$_{13}$ if q is 0, additionally embrace OH and OY; p is 1;

X and Y, independently of one another, are R$_y$; C$_2$–C$_{12}$alkyl which is substituted by R$_x$; C$_3$–C$_{30}$alkyl which is interrupted by one or more oxygen atoms and substituted by one or more of the groups OH and/or R$_x$;

R$_x$ is hydroxyl; C$_1$–C$_{12}$alkyl; C$_1$–C$_{12}$cycloalkyl; C$_1$–C$_{20}$alkoxy; C$_6$–C$_{12}$cycloalkoxy; phenyl; —OR$_z$;

R$_z$; allyl; or is C$_1$–C$_{20}$alkyl, C$_1$–C$_{20}$alkoxy or cyclohexyl each of which is substituted by hydroxyl, C$_1$–C$_{12}$alkyl, C$_1$–C$_{12}$alkoxy or carboxyl;

R$_y$ is hydrogen; C$_1$–C$_{12}$alkyl; C$_6$–C$_{12}$cycloalkyl; phenyl; R$_z$; allyl; or C$_1$–C$_{20}$alkyl or cyclohexyl each of which is substituted by hydroxyl, C$_1$–C$_{12}$alkyl, C$_1$–C$_{12}$alkoxy or carboxyl;

$R_z$ is —COR'; —COOR'; —CONR'R"; —CO—CH=CF; —CO—C(CH$_3$)=CH$_2$; R' and R", independently of one another, are hydrogen; C$_1$–C$_{20}$alkyl; C$_4$–C$_{20}$alkyl which is interrupted by oxygen; C$_4$–C$_{12}$cycloalkyl; or are C$_2$–C$_{20}$alkyl or cyclohexyl each of which is substituted by hydroxyl, C$_1$–C$_{12}$alkyl, C$_1$–C$_{12}$alkoxy or carboxyl;

especially to a mixture in which in the compound of the formula I k is 1; G$_3$, G$_4$ and G$_5$, independently of one another, are H, Cl, C$_1$–C$_8$alkyl, allyl or C$_1$–C$_4$alkoxy, especially H or methyl; G$_6$ is hydrogen; G is C$_1$–C$_{18}$alkyl or benzyl; or is C$_2$–C$_6$alkyl which is substituted by OH, C$_1$–C$_{18}$alkoxy, phenoxy, —COOG$_8$ and/or —OCOG$_{11}$; G$_8$ is C$_1$–C$_8$alkyl or C$_3$–C$_8$alkenyl; and G$_{11}$ is C$_1$–C$_4$alkyl or C$_2$–C$_3$alkenyl; and in which in the compound of the formula II R$_6$ to R$_{15}$, independently of one another, are H, C$_1$–C$_4$alkyl and Cl and R$_{11}$, R$_{12}$ and R$_{13}$, if q is 0, additionally embrace OH and OY; p is 1;

X and Y, independently of one another, are R$_y$; C$_2$–C$_{12}$alkyl which is substituted by R$_x$; C$_3$–C$_{30}$alkyl which is interrupted by one or more oxygen atoms and substituted by one or more of the groups OH and/or R$_x$;

R$_x$ is hydroxyl; C$_1$–C$_{20}$alkyl; cyclohexyl; C$_1$–C$_{20}$alkoxy; cyclohexyloxy; —OR$_z$; NHR$_z$; R$_z$; allyl;

R$_y$ is hydrogen; C$_1$–C$_{20}$alkyl; cyclohexyl;

R$_z$ is —COR'; —COOR'; —CONR'R"; —CO—CH=CH$_2$; —CO—C(CH$_3$)=CH$_2$; R' and R", independently of one another, are hydrogen; C$_1$–C$_{20}$alkyl; C$_4$–C$_{20}$alkyl which is interrupted by oxygen; cyclohexyl.

Also of very special importance are mixtures in which in the compound of the formula I k is 1; G$_3$, G$_4$ and G$_5$, independently of one another, are H, Cl, C$_1$–C$_8$alkyl, allyl or C$_1$–C$_4$alkoxy; G$_6$ is hydrogen; G is C$_1$–C$_{18}$-alkyl or benzyl; or is C$_2$–C$_6$alkyl substituted by OH, C$_1$–C$_{18}$alkoxy, phenoxy, —COOG$_8$ and/or —OCOG$_{11}$; G$_8$ is C$_1$–C$_8$alkyl or C$_3$–C$_8$alkenyl; and G$_{11}$ is C$_1$–C$_4$alkyl or C$_2$–C$_3$alkenyl; and in which in the compound of the formula 11 R$_6$ to R$_{15}$ are H; q is 1; p is 1;

X and Y, independently of one another, are R$_y$; C$_2$–C$_{12}$alkyl which is substituted by R$_x$; C$_3$–C$_{30}$alkyl which is interrupted by one or more oxygen atoms and substituted by one or more of the groups OH and/or R$_x$;

R$_x$ is hydroxyl; C$_1$–C$_{20}$alkoxy; cyclohexyloxy; —OR$_z$; R$_z$; allyl;

R$_y$ is hydrogen; C$_1$–C$_{20}$alkyl; cyclohexyl;

R$_z$ is —COR'; —COOR';

R' is hydrogen; C$_1$–C$_{20}$alkyl; C$_4$–C$_{20}$alkyl which is interrupted by oxygen; cyclohexyl or C$_1$–C$_4$alkylcyclohexyl.

The compounds of the formula I are to a large extent known; examples of known compounds include 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)4,6-bis(2,4-dimethylphenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxypropyloxy)phenyl]-4,6-bis(2,4-dimethylphenyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)4-(4-methoxyphenyl)-6-phenyl-1,3,5-triazine.

Compounds of the formula 11 are known from the publications mentioned at the outset, in particular from GB-A-2 297 091 and WO-96-28 431. Examples of known compounds include those indicated later on below, and also the compounds of Examples 1–24 of WO-96-28 431.

The preparation of the compounds of the formula I and II can take place, for example, in accordance with or in analogy to one of the methods indicated in EP-A-434 608 or in the publication by H. Brunetti and C. E. Lüthi, Helv. Chim. Acta 55, 1566 (1972), by Friedel-Crafts addition of halotriazines onto corresponding phenols. This can be followed by a further reaction, by known methods, to give compounds of the formula I or II in which G or X and, if appropriate, Y and Z are not hydrogen; such reactions and processes are described, for example, in EP-A-434 608, page 15, line 11 to page 17, line 1.

Further preparation processes, especially for compounds of the formula II, are given in WO-96-28 431 on pages 9–13.

Preparation Examples for compounds of the formula II: Abbreviations used

| | |
|---|---|
| $^1$H-NMR | proton nuclear magnetic resonance; unless otherwise stated: 300 MHz, CDCl$_3$ |
| Ethyl-Cellosolve | ethylene glycol mono ethyl ether |
| m.p. | melting point or melting range |

EXAMPLE A1

9.9 g (0.02 mol) of the compound A of the formula

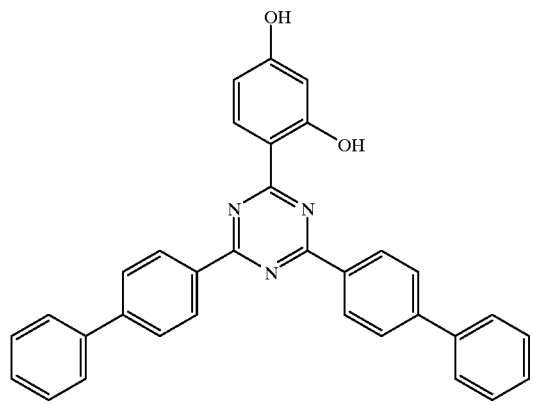

(Comp. A; preparation see WO-96-28431)

and 3 g (0.022 mol) of potassium carbonate are suspended in 50 ml of ethyl-Cellosolve. The suspenson is heated to 110° C., and 3.6 g (0.022 mol) of 1-bromohexane are added dropwise. The mixture is stirred at 110° C. for 21 hours. On cooling, a product is precipitated. The mixture is filtered and the filter residue is washed with water, to give a product of the formula

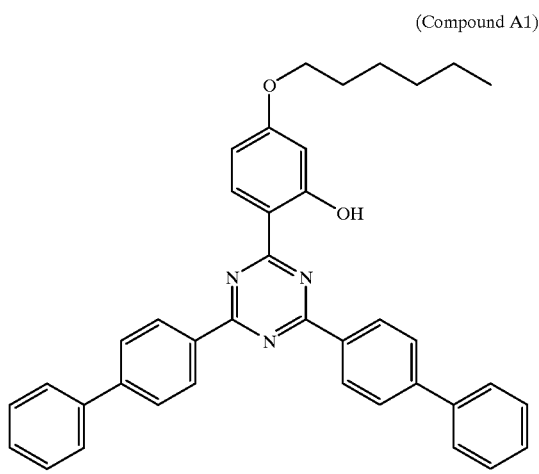

(Compound A1)

m.p.: 176–178° C.

EXAMPLE A2

8.5 g (0.0172 mol) of the compound A (see Example A1), 3.4 g (0.025 mol) of butyl glycidyl ether and 0.5 g (0.0014 mol) of ethyltriphenylphosphonium bromide are suspended in 200 ml of xylene. The mixture is heated under reflux for 17 hours. The xylene is evaporated off and the residue is recrystallized, to give 6.5 g of the compound A2 of the formula

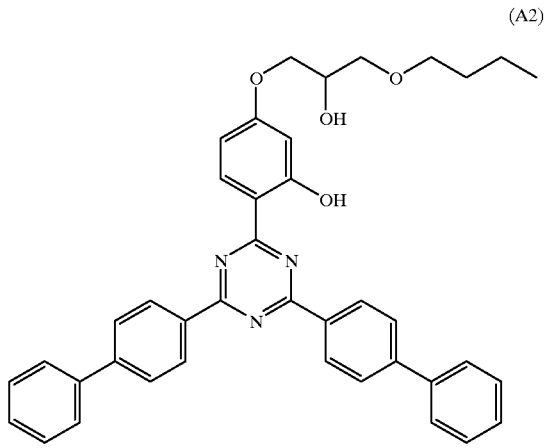

(A2)

m.p.: 156–158° C.

EXAMPLE A3

9.4 g (0.019 mol) of 2-(2,4-dihydroxyphenyl)-4,6-bis(4-biphenylyl)-1,3,5-triazine (compound A), 2.6 g (0.019 mol) of potassium carbonate and 6.1 g (0.021 mol) of octyl 2-bromopentanoate (octyl isomer mix) are suspended in 100 ml of ethyl methyl ketone. The mixture is stirred overnight at 100° C. and then filtered and the filtrate is concentrated. Chromatography over silica gel gives 6.3 g of a waxlike product of the formula

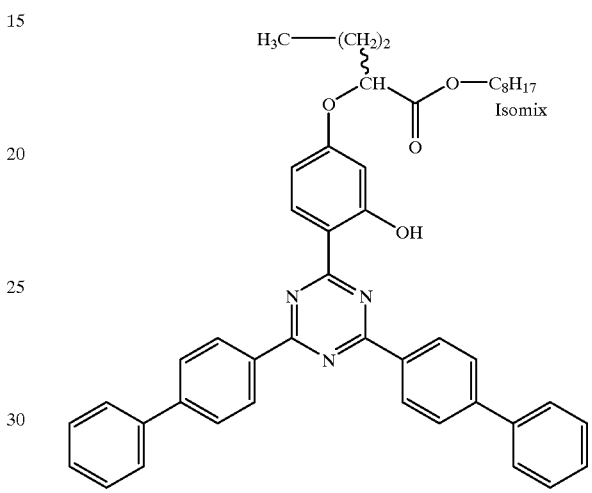

(Compound A3); $^1$H-NMR spectrum agrees with the formula.

Elemental analysis for $C_{45}H_{37}N_3O_4$:

|  | C | H | N |
| --- | --- | --- | --- |
| calculated: | 78.27 | 6.71 | 5.95 |
| found: | 79.25 | 7.18 | 5.18 |

EXAMPLES A4–A15

Further compounds of the formula II are obtained in accordance with the methods set out in Examples A1, A2 or A3 using appropriate analogous bromoalkanes, glycidyl compounds or α-brominated carboxylic esters instead of 1-bromohexane, butyl glycidyl ether or octyl 2-bromopentanoate. Structure, characterization and preparation method are compiled in the following table. Radicals labelled with n as prefix or suffix are straight-chain; (i) denotes a mixture of different alkyl isomers of the same molecular weight.

TABLE A4

Compounds of the formula

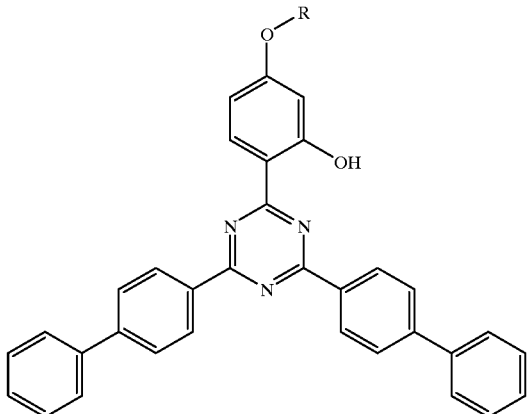

| No. | R | Preparation acc. to Ex. | m.p./° C. | Characterization |
|---|---|---|---|---|
| A4 | [cyclododecyl: CH$_2$—CH(OH)—CH$_2$—O—cyclododecyl] | A2 | 156–162 | $^1$H-NMR |
| A5 | CH(n-C$_3$H$_7$)—COO—C$_2$H$_5$ | A3 | 168–171 | $^1$H-NMR |
| A6 | CH$_2$•CH(OH)—CH$_2$—(OCH$_2$CH$_2$)$_3$—O—C$_4$H$_9$(n) | A2 | | $^1$H-NMR |
| A7 | CH$_2$•CH(OH)—CH$_2$—(OCH$_2$CH$_2$)$_2$—OCH$_3$ | A2 | 107–110 | $^1$H-NMR |
| A8 | CH$_2$CH(C$_2$H$_5$)—C$_4$H$_9$(n) | A1 | 63–70 | $^1$H-NMR |
| A9 | CH$_2$COO—C$_8$H$_{17}$(i) | A3 | 140–142 | $^1$H-NMR |
| A10 | CH$_2$•CH(OH)—CH$_2$—OC(O)—C(C$_x$H$_{2x+1}$)(C$_y$H$_{2y+1}$)(C$_z$H$_{2z+1}$)<br>in which x,y and z are each from the range 1–6 and x + y + z = 8 | A2 | 156–158 | $^1$H-NMR |
| A11 | CH$_2$•CH(OH)—CH$_2$—OCH$_2$—CH(C$_2$H$_5$)•(CH$_2$)$_3$CH$_3$ | A2 | 142–143 | $^1$H-NMR |
| A12 | CH(n-C$_6$H$_{13}$)—COO—C$_2$H$_5$ | A3 | 157–159 | $^1$H-NMR |
| A13 | CH(CH$_3$)—COO—C$_2$H$_5$ | A3 | 177–178 | $^1$H-NMR |
| A14 | CH(CH$_3$)—COO—C$_8$H$_{17}$(i) | A3 | 60–70 | $^1$H-NMR |
| A15 | CH(n-C$_4$H$_9$)—COO—CH$_3$ | A3 | 182–183 | $^1$H-NMR |
| A16 | CH$_2$•CH(OH)—CH$_2$—O—(2,2,6,6-tetramethyl-1-methylpiperidin-4-yl) | A2 | 105 | $^1$H-NMR |

TABLE A4-continued

Compounds of the formula

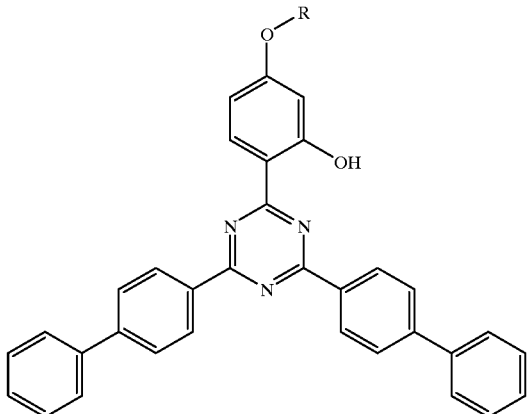

| No. | R | Preparation acc. to Ex. | m.p./° C. | Characterization |
|---|---|---|---|---|
| A17 | CH(n-C$_3$H$_7$)—COO—C$_2$H$_5$ | A3 | 168–171 | $^1$H-NMR |

EXAMPLE A18

30 g (48 mmol) of the compound A17 are stirred at 100° C. for 2 h together with 3.4 g (60 mmol) of finely powdered KOH in 300 ml of ethyl-Cellosolve. Then 100 ml of acetic acid are added and the product precipitates. The precipitate is filtered off and recrystallized from ethyl-Cellosolve, to give the free acid (m.p. 196–198° C.) of the formula

EXAMPLE A19

20 g (34 mmol) of the acid from Example A18 are suspended in 200 ml of toluene and then 11.9 g (100 mmol) of thionyl chloride are added. Following the addition of a few drops of dimethylformamide, the reaction mixture is held at reflux temperature for 2 h and the solvent is evaporated off, to give the compound 2,4-bis(4-phenylphenyl)-6-(2-hydroxy-4-[1-chlorocarbonyl]-butyloxyphenyl)-1,3,5-triazine. To this crude product there are added 50 ml of dichloromethane, whereupon a clear solution is formed. Then 3.2 g (100 mmol) of methanol and 10.1 g (100 mmol) of triethylamine are added, and the mixture is allowed to stand at room temperature for 5 h. The reaction mixture is concentrated by evaporation and the product is chromatographed over silica gel, to give the compound of the formula

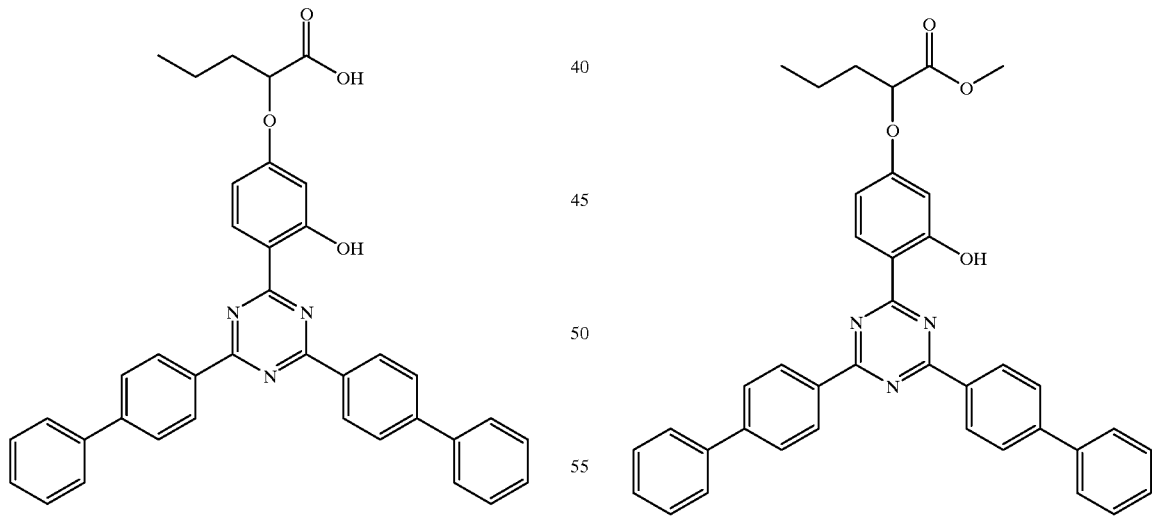

of m.p. 177–180° C.

EXAMPLES A20–A30

Further compounds of the formula II are obtained in accordance with Example A19 by esterifying the free acid. Structure, characterization and preparation method are compiled in the following table. Radicals labelled with n as prefix or suffix are straight-chain; (i) denotes a mixture of different alkyl isomers of the same molecular weight.

TABLE A20

Compounds of the formula

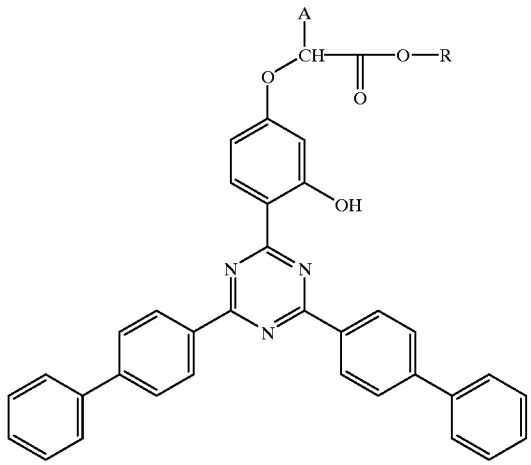

| No. | A | R | m.p./° C. | Characterization |
|---|---|---|---|---|
| A20 | n-propyl | methylcyclohexyl | 174–179 | $^1$H-NMR |
| A21 | n-propyl | CH$_2$CH(C$_2$H$_5$)—C$_2$H$_5$ | | $^1$H-NMR |
| A22 | n-propyl | CH$_2$CH(CH$_3$)—C$_2$H$_5$ | | $^1$H-NMR |
| A23 | n-propyl | CH(CH$_3$)—CH$_2$—CH(CH$_3$)—CH$_3$ | 85–97 | $^1$H-NMR |
| A24 | n-propyl | CH$_2$—C(CH$_3$)$_3$ | 143–145 | $^1$H-NMR |
| A25 | n-propyl | CH$_2$—CH$_2$—CH(CH$_3$)—CH$_3$ | 152–154 | $^1$H-NMR |
| A26 | n-propyl | n-C$_8$H$_{17}$ | | $^1$H-NMR |
| A27 | n-propyl | n-C$_7$H$_{15}$ | 78–82 | $^1$H-NMR |
| A28 | ethyl | ethyl | 165–167 | $^1$H-NMR |
| A29 | n-butyl | C$_8$H$_{17}$(i) | wax | $^1$H-NMR: $\delta$ = 13.52 ppm (s, 1H) $\delta$ = 8.61 ppm (s, 4H) $\delta$ = 6.59 ppm (d, 1H) |
| A30 | ethyl | C$_8$H$_{17}$(i) | wax | $^1$H-NMR: $\delta$ = 13.54 ppm (s, 1H) $\delta$ = 8.61 ppm (s, 4H) $\delta$ = 6.65 ppm (d, 1H) |

The novel mixtures can be obtained from the individual compounds of the formulae I and II by methods known in the art, for example by mixing, conjoint milling or cocrystallization. Mixing by incorporation of the compounds of the formulae I and II into the substrate to be stabilized is also possible; in this case the individual compounds can be incorporated simultaneously or in succession, for example by coextrusion.

The novel mixture comprising compounds of the formulae I and II798 can be used as a stabilizer for organic materials against damage by light, oxygen or heat. The novel compounds are especially suitable as light stabilizers (UV absorbers).

Particular advantages of the novel mixture are, inter alia, the outstanding resistance of the stabilized material to the influences of weathering and light, and the outstanding photostability of the incorporated stabilizer mixture. Also worthy of mention is the excellent substrate compatibility of the novel mixture.

The materials to be stabilized can, for example, be oils, fats, waxes, cosmetics or biocides. Particular interest attaches to use in polymeric materials, as in plastics, rubbers, coating materials, photographic materials or adhesives.

Examples of polymers and other substrates which can be stabilized in this way are the following:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IV*b*, V*b*, VI*b* or VIII of the Periodic Table. These metals usually have one or more than one ligand, typically oxides, halides, alcoholates, esters, ethers, amines, alkyls, alkenyls and/or aryls that may be either π or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups I$a$, II$a$ and/or III$a$ of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/-vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

The invention therefore also provides a composition comprising

A) an organic material which is sensitive to damage by light, oxygen and/or heat, and B) as stabilizer, a mixture comprising a compound of the formula I and a compound of the formula II.

The invention also provides a method of stabilizing organic material against damage by light, oxygen and/or heat, which comprises adding to said material, as stabilizer, a mixture comprising a compound of the formula I and a compound of the formula II, and provides for the use of a mixture comprising a compound of the formula I and a compound of the formula II for stabilizing organic material.

The amount of stabilizer to be used depends on the organic material to be stabilized and on the intended use of the stabilized material. In general the novel composition comprises from 0.01 to 15, in particular from 0.05 to 10 and, especially, from 0.1 to 5 parts by weight of the stabilizer (component B) per 100 parts by weight of component A.

The stabilizer (component B) can also be a mixture of three or more compounds, provided that at least one compound of the type of the formula I and at least one compound of the type of the formula II are present. In addition to the novel mixture of compounds, the novel compositions may also include other stabilizers or any other additives, for example antioxidants, further light stabilizers, metal passivators, phosphites or phosphonites. Examples thereof are the following stabilizers:

1. Antioxidants 1.1. Alkylated monophenols, for example 2,6-di-tert-butyl-4-methylphenol, 2-tert-butyl-4,6-di-methylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4, 6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl) phenol, 2,4-di-methyl-6-(1'-methylheptadec-1'-yl)phenol, 2,4-dimethyl-6-(1'-methyltridec-1'-yl) phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxy-phenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl)disulfide.

1.6. Alkylidenebisphenols, for example 2,2'-methylenebis (6-tert-butyl-4-methylphenol), 2,2'-methylenebis(6-tertbutyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butyl-phenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl) dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3, 5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl)pentane.

1.7. O- , N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris (3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl) malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis (3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis (octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris (3,5-di-tert-butyl-4-hydroxyphenoxy)-1,2,3-triazine, 1,3,5-tris-(3,5-di-tert-butyl-4-hydroxybenzyl)isocyanurate, 1,3,5-tris (4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylol-propane, 4-hydroxymethyl-1-phospha-2,6,7-trioxabicyclo[2.2.2] octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexane-diol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3.5-dicyclohexyl-4-hydroxyphenyl) prolionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxaphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis (3,5-di-tert-butyl-4-hydroxyphenylpropionyl) trimethylenediamide, N,N'-bis(3,5-di-tert-butyl-4-hydroxyphenylpropionyl)-hydrazide, N,N'-bis[2-(3-[3,5-di-tert-butyl-4-hydroxyphenyl]propionyloxy)ethyl]oxamide (Naugard®XL-1 supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p- phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenlenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxy-diphenylamine, N-phenyl-1-naphthylamine, N-(4-tert-octylphenyl)-1-naphthylamine, N-phenyl-2-naphthylamine, octylated diphenylamine, for example p,p'-di-tert-octyidiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyidiphenylamines, a mixture of mono- and dialkylated nonyidiphenylamines, a mixture of mono- and dialkylated dodecyldiphenylamines, a mixture of mono- and dialkylated isopropyl/isohexyldiphenylamines, a mixture of mono- und dialkylated tert-butyidiphenylamines, 2,3-dihydro-3,3-dimethyl-4H-1,4-benzothiazine, phenothiazine, a mixture of mono- und dialkylated tert-butyl/tert-octylphenothiazines, a mixture of mono- und dialkylated tert-octyl-phenothiazines, N-allylphenothiazin, N,N,N',N'-tetraphenyl-1,4-diaminobut-2-ene, N,N-bis-(2,2,6,6-tetramethyl-piperid-4-yl-hexamethylenediamine, bis(2,2,6,6-tetramethylpiperid-4-yl)-sebacate, 2,2,6,6-tetramethylpiperidin-4-one, 2,2,6,6-tetramethylpiperidin-4-ol.

2. UV absorbers and light stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-($\alpha,\alpha$-dimethylbenzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl)phenylbenzotriazole, 2,2'-methylene-bis-[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—$CH_2CH_2$—COO—$CH_2CH_2$]$_2$ where R=3'-tert-butyl-4'-hydroxy-5'-2H-benzotriazol-2-ylphenyl, 2-[2'-hydroxy-3'-($\alpha,\alpha$-dimethylbenzyl)-5'-(1,1,3,3-tetramethylbutyl)-phenyl]benzotriazole; 2-[2'-hydroxy-3'-(1,1,3,3-tetramethylbutyl)-5'-($\alpha,\alpha$-dimethylbenzyl)-phenyl]benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis (4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl $\alpha$-cyano-$\beta,\beta$-diphenylacrylate, isooctyl $\alpha$-cyano-$\beta,\beta$-diphenylacrylate, methyl $\alpha$-carbomethoxycinnamate, methyl $\alpha$-cyano-$\beta$-methyl-p-methoxy-cinnamate, butyl $\alpha$-cyano-$\beta$-methyl-p-methoxy-cinnamate, methyl $\alpha$-carbomethoxy-p-methoxycinnamate and N-($\beta$-carbomethoxy-$\beta$-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis-(2,2,6,6-tetramethyl-4-piperidyl)-1,2,3,4-butane-tetracarboxylate, 1,1'-(1,2-ethanediyl)-bis-(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dione, bis(1-octyloxy-2,2,6,6-tetramethylpiperidyl) sebacate, bis(1-octyloxy-2,2,6,6-tetramethylpiperidyl) succinate, linear or cyclic condensates of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6- di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis (2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro [4,5]decane, a reaction product of 7,7,9,9-tetramethyl-2-cycloundecyl-1-oxa-3,8-diaza-4-oxospiro [4,5]decane und epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl) hexamethylenediamine, diester of 4-methoxymethylene-malonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-di-benz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 2,2',2"-nitrilo[triethyltris(3,3',5,5'-tetra-tert-butyl-1,1'-biphenyl-2,2'-diyl)phosphite], 2-ethylhexyl(3,3',5,5'-tetra-tert-butyl-1,1'-biphenyl-2,2'-di-yl)phosphite.

Especially preferred are the following phosphites:

Tris(2,4-di-tert-butylphenyl) phosphite (Irgafos®168, Ciba-Geigy), tris(nonylphenyl) phosphite,

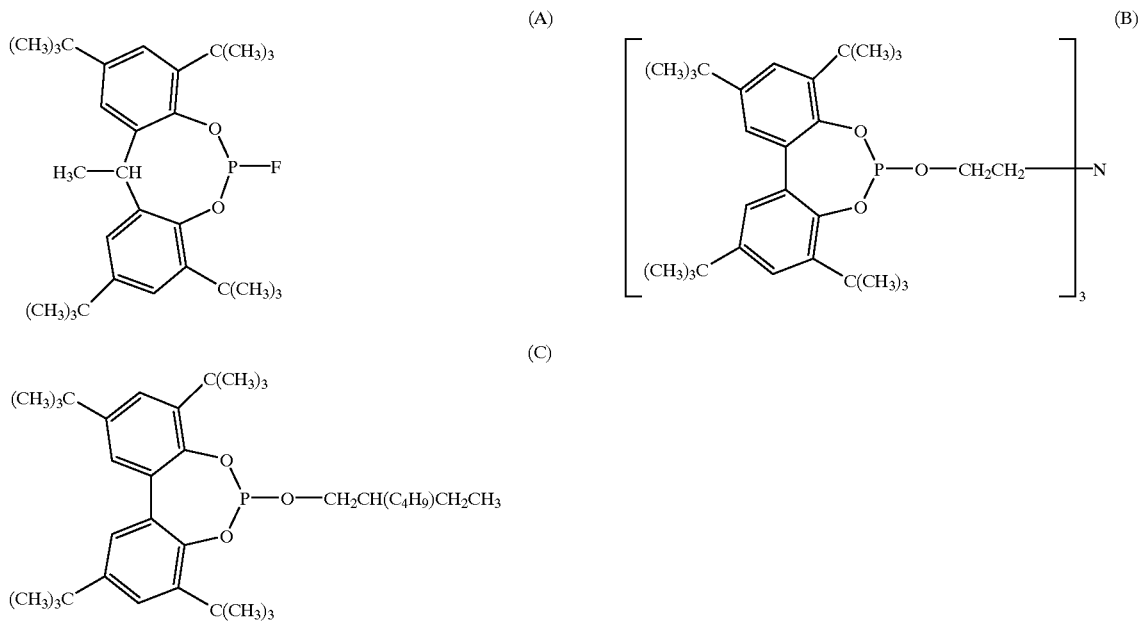

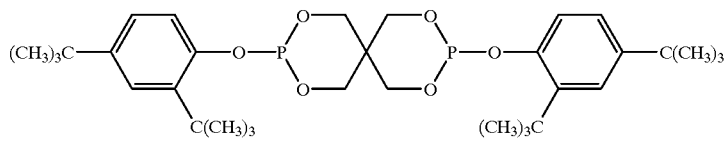
(D)

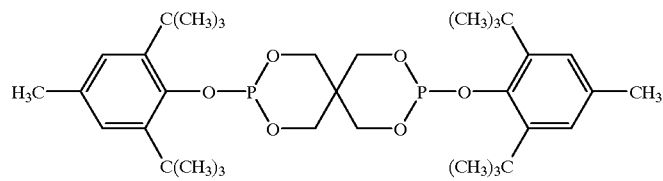
(E)

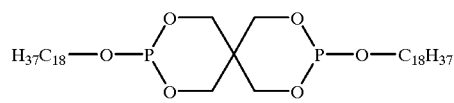
(F)

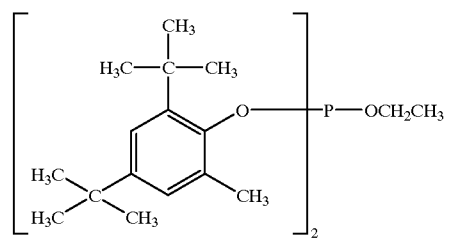
(G)

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridcyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyidithiocarbamate, dioctadecyl disulfide, pentaerythritol tetrakis (β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zink pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A-0591102 or 3-[4-(2-acetoxyethoxy)-phenyl]-5,7-di-tert-butyl-benzofuran-2-one, 5,7-di-tert-butyl-3-[4-(2-stearoyloxyethoxy)phenyl] benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one. The nature and the amount of the other stabilizers added are determined by the nature of the substrate to be stabilized and its intended use; in many cases from 0.1 to 5% by weight is used, based on the polymer to be stabilized.

With particular advantage the novel stabilizer mixtures can be employed in compositions which comprise as component A a synthetic organic polymer, in particular a thermoplastic polymer, a binder for coatings such as paints, for example, or a photographic material. Examples of suitable thermoplastic polymers are polyolefins and polymers which contain heteroatoms in the main chain. Preference is also given to those compositions in which component A is a thermoplastic polymer which contains nitrogen, oxygen and/or sulfur, especially nitrogen or oxygen, in the main chain. Examples of such polymers are the following classes of thermoplastic polymers:

1. Polyacetals, such as polyoxymethylene, and those polyoxymethylenes which comprise comonomers, for example ethylene oxide; polyacetals which are modified with thermoplastic polyurethanes, acrylates or MBS.
2. Polyphenylene oxides and sulfides and mixtures thereof with styrene polymers or polyamides.
3. Polyamides and copolyamides, for example those derived from diamines and dicarboxylic acids and/or from aminocarboxylic acids or the corresponding lactams, such as polyamide 4, polyamide 6, polyamide 6/6, 6/10, 6/9, 6/12, 4/6, polyamide 11, polyamide 12, aromatic polyamides based on m-xylene, diamine and adipic acid; polyamides prepared from hexamethylenediamine and iso- and/or terephthalic acid with or without an elastomer as modifier, for example poly-2,4,4-trimethylhexamethyleneterephthalamide, poly-m-phenyleneisophthalamide. Block copolymers of the abovementioned polyamides with polyolefins, olefin copolymers, ionomers or chemically bonded or grafted elastomers; or with polyethers, for example with polyethylene glycol, polypropylene glycol or polytetramethylene glycol. In addition, copolyamides or polyamides modified with EPDM or ABS; and polyamides condensed during processing (RIM polyamide systems).
4. Polyureas, polyimides, polyamideimides and polybenzimidazoles.
5. Polyesters, for example those derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate, polyhydroxybenzoates, and also block polyether-esters derived from polyethers having hydroxyl end groups; and also polyesters modified with polyearbonates or MBS.
6. Polycarbonates and polyester carbonates, especially aromatic polycarbonates, for example those based on 2,2-bis(4-hydroxyphenyl)propane or 1,1-bis(4-hydroxyphenyl)cyclohexane.
7. Polysulfones, polyether sulfones and polyether ketones, especially aromatic polymers of this class.
8. Mixtures (polyblends) of such polymers with one another or with other polymers, for example with polyolefins, polyacrylates, polydienes or other elastomers as impact modifiers.

Among these preference is given to the polycarbonates, polyesters, polyamides, polyacetals, polyphenylene oxides and polyphenylene sulfides, but especially to the polycarbonates. These are in particular those polymers whose constitutional repeating unit is of the formula —[O—A—O—CO]— in which A is a divalent phenolic radical. Examples of A are given, inter alia, in US Pat. No. 4,960,863 and DE-A-3 922 496.

The polymers of component (A) can be linear or branched. Shaping of these polymers takes place at a relatively high temperature; polycarbonate, for example, is injection moulded at 220–330° C. At these temperatures, the majority of the customary light stabilizers and antioxidants are unstable and begin to decompose. The abovementioned mixtures, however, are extremely temperature-stable and are therefore particularly suitable for stabilizing the polymers mentioned.

Also of interest are compositions in which component (A) is a polyolefin, for example polyethylene or polypropylene.

Incorporation into the organic polymers, for example into the synthetic organic, especially thermoplastic polymers, can take place by adding the novel mixtures, with or without any further additives, by the methods customary in the art. They can be incorporated judiciously prior to or during the shaping operation, for example by mixing the pulverulent components or by adding the stabilizer to the melt or solution of the polymer, or by applying the dissolved or dispersed compounds to the polymer, with or without subsequent evaporation of the solvent. In the case of elastomers these can also be stabilized as latices. Another possibility for incorporating the novel mixtures into polymers is to add them prior to or during the polymerization of the corresponding monomers and/or prior to crosslinking.

The novel mixtures can also be added in the form of a master batch which contains these compounds in a concentration, for example, of 2.5 to 25% by weight to the polymers that are to be stabilized.

The novel mixtures can judiciously be incorporated by the following methods:

as an emulsion or dispersion (e.g. to latices or emulsion polymers)
as a dry mixture during the mixing of additional components or polymer mixtures
by direct addition to the processing apparatus (for example extruders, internal mixers, etc.)
as a solution or melt.

The stabilized polymer compositions thus obtained can be converted by the customary methods, for example by hot pressing, spinning, extrusion or injection moulding, into shaped articles, for example fibres, films, strips, sheets, sandwich boards, vessels, pipes and other profiles.

The invention therefore additionally provides for the use of the novel polymer composition for producing a shaped article.

Also of interest is the use in multilayer systems. In this case a novel polymer composition having a relatively high content of novel stabilizer, for example 5–15% by weight, is applied in a thin film (10–100 $\mu$m) to a shaped article made from a polymer containing little or no stabilizer of formula I. Application can be made at the same time as the shaping of the base article, for example by coextrusion. Alternatively, application can be made to the ready-shaped base article, for example by lamination with a film or by coating with a solution. The external layer or layers of the finished article has or have the function of a UV filter which protects the interior of the article against UV light. The external layer contains preferably 5–15% by weight, especially 5–10% by weight, of at least one compound of the formula I and one compound of the formula II.

The polymers stabilized in this way feature high weathering stability, especially high stability to UV light. As a result, even during long-term outdoor service, they retain their mechanical properties and also their colour and their gloss.

Of particular interest is the use of the novel mixture of compounds as stabilizer for coatings, for example for paints. The invention therefore also provides those compositions whose component A is a film-forming binder.

The novel coating composition preferably contains 0.01–10 parts by weight, in particular 0.05–10 parts by weight, and especially 0.1–5 parts by weight of the novel stabilizer B per 100 parts by weight of solid binder A.

Also possible here are multilayer systems where the concentration of the novel stabilizer (component B) in the top layer can be higher, for example from 1 to 15 parts by weight, especially 3–10 parts by weight of B per 100 parts by weight of solid binder A. Such multilayer systems can, for example, be 2- or 3-coat finishes.

The use of the novel mixture of compounds as a stabilizer in coatings brings with it the additional advantage that delamination, i.e. the peeling of the coating from the substrate, is prevented. This advantage is particularly important in the case of metallic substrates, including multilayer systems on metallic substrates.

The binder (component A) can in principle be any binder which is customary in the art, for example those described in *Ullmann's Encyclopedia of Industrial Chemistry,* 5th Ed., Vol. A18, pp. 368–426, VCH, Weinheim 1991. In general it is a film-forming binder based on a thermoplastic or thermosetting resin, predominantly on a thermosetting resin. Examples thereof are alkyd, acrylic, polyester, phenolic, melamine, epoxide and polyurethane resins and mixtures thereof.

Component A can be a cold-curable or a hot-curable binder; the addition of a curing catalyst may be advantageous. Suitable catalysts which accelerate the curing of the binder are, for example, described in *Ullmann's Encyclopedia of Industrial Chemistry,* Vol. A18, p.469, VCH Verlagsgesellschaft, Weinheim 1991.

Preference is given to coating compositions in which component A is a binder comprising a functional acrylate resin and a crosslinker.

Examples of coating compositions with specific binders are:

1. paints based on cold- or hot-crosslinkable alkyd, acrylate, polyester, epoxy or melamine resins or mixtures of such resins with or without an added curing catalyst;
2. two-component polyurethane paints based on hydroxyl-containing acrylate, polyester or polyether resins and on aliphatic or aromatic isocyanates, isocyanurates or polyisocyanates;
3. one-component polyurethane paints based on blocked isocyanates, isocyanurates or polyisocyanates, which are unblocked in the course of baking;
4. one-component polyurethane paints based on aliphatic or aromatic urethanes or polyurethanes and on hydroxyl-containing acrylate, polyester or polyether resins;
5. one-component polyurethane paints based on aliphatic or aromatic urethane acrylates or polyurethane acrylates having free amine groups in the urethane structure and on melamine resins or polyether resins, with or without an added curing catalyst;
6. two-component paints based on (poly)ketimines and aliphatic or aromatic isocyanates, isocyanurates or polyisocyanates;
7. two-component paints based on (poly)ketimines and on an unsaturated acrylate resin or polyacetoacetate resin or methyl methacrylamidoglycolate;
8. two-component paints based on carboxyl- or amino-containing polyacrylates and polyepoxides;
9. two-component paints based on acrylate resins containing anhydride groups and on a polyhydroxy or polyamino component;
10. two-component paints based on acrylate-containing anhydrides and polyepoxides;
11. two-component paints based on (poly)oxazolines and on acrylate resins containing anhydride groups or on unsaturated acrylate resins, or aliphatic or aromatic isocyanates, isocyanurates or polyisocyanates;
12. two-component paints based on unsaturated polyacrylates and polymalonates;
13. thermoplastic polyacrylate paints based on thermoplastic acrylate resins or externally crosslinking acrylate resins in combination with etherified melamine resins;
14. paint systems based on siloxane-modified or fluorine-modified acrylate resins.

In addition to components A and B the novel coating composition comprises as component C a light stabilizer of the sterically hindered amine and/or 2-hydroxyphenyl-2H-benzotriazole type, for example as set out in the above list under items 2.1, 2.6. Of particular industrial interest in this context is the addition of 2-hydroxyphenyl-2H-benzotriazoles.

In order to achieve maximum light stability, it is of particular interest to add sterically hindered amines, as set out in the above list under 2.6. The invention therefore also provides a coating composition which, in addition to components A and B, comprises, as component C, a light stabilizer of the sterically hindered amine type.

This is preferably a 2,2,6,6-tetraalkylpiperidine derivative containing at least one group of the formula

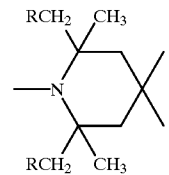

in which R is hydrogen or methyl, especially hydrogen.

Component C is preferably used in an amount of 0.05–5 parts by weight per 100 parts by weight of solid binder.

Examples of tetraalkylpiperidine derivatives which can be used as component C are given in EP-A-356 677, pages 3–17, Sections a) to f). Those sections of that EP-A are regarded as part of the present description. It is particularly judicious to employ the following tetraalkylpiperidine derivatives:

bis(2,2,6,6-tetramethylpiperidin-4-yl) succinate,
bis(2,2,6,6-tetramethylpiperidin-4-yl) sebacate,
bis(1,2,2,6,6-pentamethylpiperidin-4-yl) sebacate,
di-(1,2,2,6,6-pentamethylpiperidin-4-yl) butyl(3,5-di-tert-butyl-4-hydroxybenzyl)malonate,
bis(1-octyloxy-2,2,6,6-tetramethylpiperidin-4-yl) sebacate,
tetra(2,2,6,6-tetramethylpiperidin-4-yl) butane-1,2,3,4-tetracarboxylate,
tetra(1,2,2,6,6-pentamethylpiperidin-4-yl) butane-1,2,3,4-tetracarboxylate,
2,2,4,4-tetramethyl-7-oxa-3,20-diaza-21-oxo-dispiro [5.1.11.2]heneicosane,
8-acetyl-3-dodecyl-1,3,8-triaza-7,7,9,9-tetramethylspiro [4.5]decane-2,4-dione,
1,1-bis(1,2,2,6,6-pentamethylpiperidin-4-yl-oxycarbonyl)-2-(4-methoxyphenyl)ethene,
or a compound of the formulae

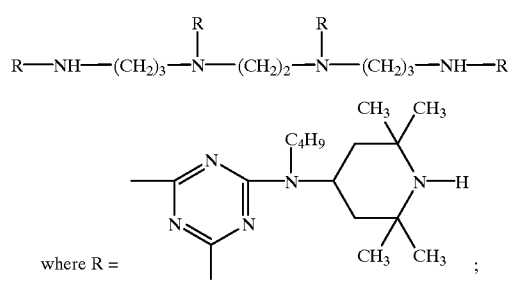

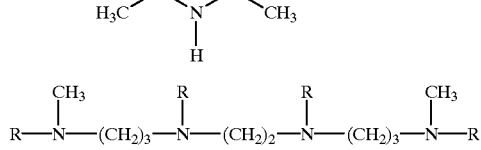

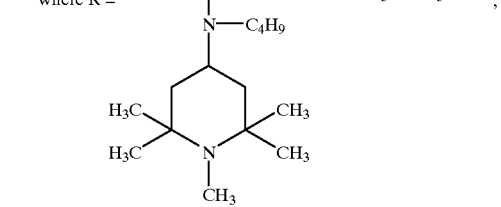

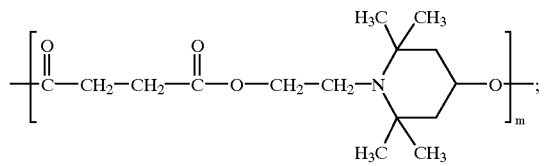

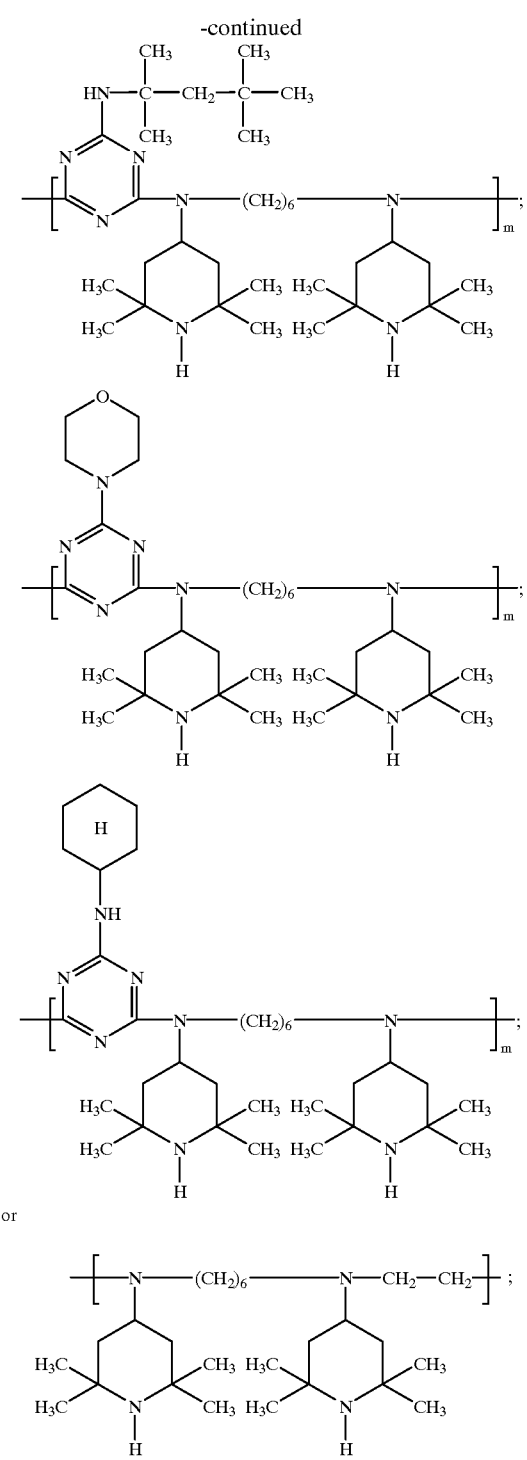

where m is 5–50.

In addition to components A, B and, if present, C, the coating composition can comprise further components, for example solvents, pigments, dyes, plasticizers, stabilizers, thixotropic agents, drying catalysts and/or levelling assistants. Examples of possible components are those as described in *Ullmann's Encyclopedia of Industrial Chemistry*, 5th Ed., Vol. A18, pp. 429–471, VCH, Weinheim 1991.

Possible drying catalysts or curing catalysts are, for example, organometallic compounds, amines, amines, amino-containing resins and/or phosphines. Examples of organometallic compounds are metal carboxylates, especially those of the metals Pb, Mn, Co, Zn, Zr or Cu, or metal chelates, especially those of the metals Al, Ti or Zr, or organometallic compounds such as organotin compounds, for example.

Examples of metal carboxylates are the stearates of Pb, Mn or Zn, the octoates of Co, Zn or Cu. the naphthenates of Mn and Co or the corresponding linoleates, resinates or tallates.

Examples of metal chelates are the aluminium, titanium or zirconium chelates of acetylacetone, ethyl acetylacetate, salicylaldehyde, salicylaldoxime, o-hydroxyacetophenone or ethyl trifluoroacetylacetate and the alkoxides of these metals.

Example of organotin compounds are dibutyltin oxide, dibutyltin dilaurate or dibutyltin dioctoate.

Examples of amines are especially tertiary amines, for example tributylamine, triethanolamine, N-methyldiethanolamine, N-dimethylethanolamine, N-ethylmorpholine, N-methylmorpholine or diazabicyclooctane (triethylenediamine) and also salts thereof. Further examples are quaternary ammonium salts, for example trimethylbenzylammonium chloride.

Amino-containing resins are simultaneously binder and curing catalyst. Examples thereof are amino-containing acrylate-copolymers.

The curing catalyst used can also be a phosphine, for example triphenylphosphine.

The novel coating compositions can also be radiation-curable coating compositions. In this case the binder consists essentially of monomeric or oligomeric compounds having ethylenically unsaturated bonds (prepolymers) which following application are cured, i.e. converted to a crosslinked, high molecular mass form, by means of actinic radiation. If the system is a UV-curing system, it generally also includes a photoinitiator. Corresponding systems are described in the abovementioned publication *Ullmann's Encyclopedia of Industrial Chemistry*, 5th Ed., Vol.A18, pages 451–453. In radiation-curable coating compositions the novel stabilizers can be employed even without the addition of sterically hindered amines.

The novel coating compositions can be applied to any desired substrates, for example to wood, metal, plastic or ceramic materials. They are preferably used as a topcoat in the finishing of cars. Where the topcoat consists of two coats of which the bottom coat is pigmented and the upper coat is not pigmented, the novel coating composition can be used for the upper or bottom coat or for both coats, but preferably for the upper coat.

The novel coating compositions can be applied to the substrates by the customary techniques, for example by spreading, spraying, flow coating, dipping or electrophoresis; see also *Ullmann's Encyclopedia of Industrial Chemistry*, 5th Ed., Vol.A18, pp. 491–500.

The curing of the coatings can—depending on the binder system—be carried out at room temperature or by heating. It is preferred to cure the coatings at 50–150° C., powder coatings also at higher temperatures.

The coatings obtained in accordance with the invention have outstanding resistance to the damaging effects of light, oxygen and heat; particular mention should be made of the good light and weathering resistance of the resulting coatings, for example paints.

The invention therefore also provides a coating, especially a paint, which is stabilized against the damaging effects of light, oxygen and heat by virtue of the addition of the above-described novel mixture of compounds. The paint is preferably an automotive topcoat. The invention additionally comprises a method of stabilizing a coating based on organic polymers against damage by light, oxygen and/or heat, which comprises admixing to the coating composition a mixture comprising compounds of the formula I and II, and provides for the use of a mixture comprising compounds of the formula I and II in coating compositions as stabilizers against damage by light, oxygen and/or heat.

The coating compositions can include an organic solvent or solvent mixture in which the binder is soluble. The coating composition can also be, however, an aqueous solution or dispersion. The vehicle can also be a mixture of an organic solvent and water. The coating composition can also be a high-solids paint or can be solvent-free (for example a powder coating). Powder coatings are those, for example, as described in *Ullmann's Encyclopedia of Industrial Chemistry*, 5th Ed., A18, pages 438–444. The powder coating can also be present in the form of a powder slurry, i.e. a dispersion of the powder in, preferably, water.

The pigments can be inorganic, organic or metallic pigments. The novel coating compositions preferably comprise no pigments and are used as a clearcoat.

Preference is likewise given to the use of the novel coating composition as a topcoat for applications in the automotive industry, especially as a pigmented or unpigmented topcoat of the paint system. However, its use for underlying coats is also possible. In such systems the novel mixture can also be employed such that one component is present in the topcoat (for example in the clearcoat) and the other component in an underlying coat (for example in the basecoat). An example would be a paint system in which the topcoat comprises a compound of the formula II and an underlying coat comprises a compound of the formula I.

The following compounds are examples of individual compounds of the formula I: 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis (2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis (2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy) phenyl]-4,6-bis(2,4-dimethyl)-1,3,5triazine, 2-[2-hydroxy-4-(2-hydroxy-3-octyloxy-propyloxy)phenyl]-4,6-bis(2,4-dimethyl)-1,3,5-triazine, 2-[4-(dodecyloxytridecyloxy-2-hydroxypropoxy)-2-hydroxy-phenyl]-4,6-bis (2,4-dimethylphenyl)-1,3,5-triazine, 2-[2-hydroxy-4-(2-hydroxy-3-dodecyloxy-propoxy)phenyl]4,6-bis(2,4-dimethylphenyl)-1,3,5-triazine, 2-(2-hydroxy-4-hexyloxy)

phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}4,6-bis(2,4-dimethylphenyl)-1,3,5-triazine, compounds of the type:

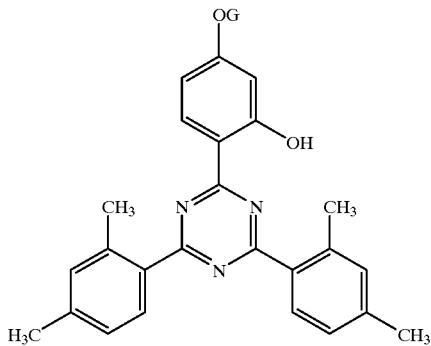

| Compound No. | G |
|---|---|
| I/1 | $C_8H_{17}$ |
| I/2 | $CH_2$—$CH(OH)$—$CH_2$—O—$C_{12}H_{25}$ |
| I/3 | $CH_2$—$CH(OH)$—$CH_2$—O—$C_{13}H_{27}$ |
| I/8 | $CH_2$—$CH(OH)$—$CH_2$—O—$CH_2$—$CH(C_2H_5)$—$C_4H_9$ |
| I/9 | $CH_2$—CO—O—$CH_2$—$CH(CH_3)$—$C_3H_7$ |
| I/10 | $CH_2$—CO—O—$C_4H_9$ |
| I/11 | $CH_2$—CO—O—$C_8H_{17}(i)$ |
| I/12 | $CH_2$—CO—O—$(CH_2CH_2O)_n$-H, n = 7 |
| I/13 | $CH_2$—CO—O—$CH_2CH(CH_3)OCH_2CH(CH_3)OCH_2CH(CH_3)CH_3$ |
| I/14 | $CH_2$—CO—O—$(CH_2CH_2O)_n$-H, n = 9 | and compounds of the type:

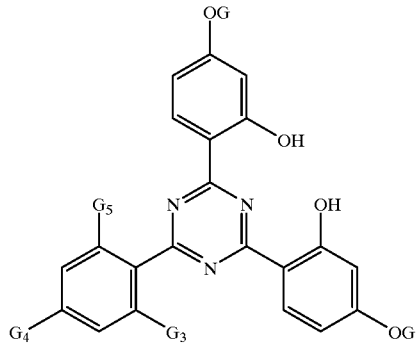

| Compound No. | G | $G_3$ | $G_4$ | $G_5$ |
|---|---|---|---|---|
| I/4 | $CH_2$—$CH(OH)$—$CH_2$—O—$C_{12}H_{25}$ | $CH_3$ | $CH_3$ | H |
| I/5 | $CH_2$—$CH(OH)$—$CH_2$—O—$C_{13}H_{27}$ | $CH_3$ | $CH_3$ | H |
| I/6 | $CH_2$—$CH(OH)$—$CH_2$—O—$C_{12}H_{25}$ | $CH_3$ | $CH_3$ | $CH_3$ |
| I/7 | $CH_2CH(OH)CH_2OCH_2CH(C_2H_5)C_4H_9$ | OH | OG | H |

The following compounds are examples of individual compounds of the formula II:

Compounds of the type:

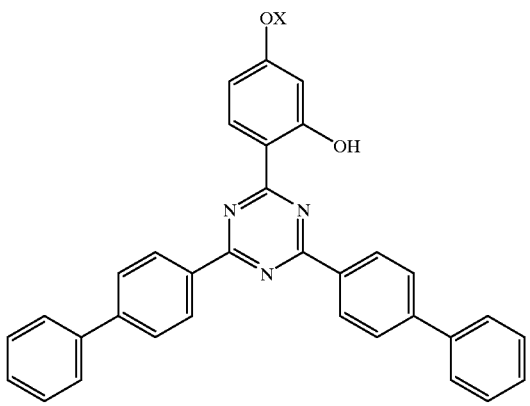

| Compound No. | X | |
|---|---|---|
| II/1 | CH$_2$—CH(OH)—CH$_2$—O—C$_{12}$H$_{25}$ | |
| II/2 | CH$_2$—CH(OH)—CH$_2$—O—C$_{13}$H$_{27}$ | |
| II/3 | CH(C$_4$H$_9$)—CO—O—C$_8$H$_{17}$(i) | (cmpd. of example A29) |
| II/4 | CH$_2$CH(OH)CH$_2$—O—(CH$_2$CH$_2$O)$_3$—C$_4$H$_9$ | |
| II/5 | CH(CH$_3$)—CO—O—C$_8$H$_{17}$(i) | (cmpd. of example A14) |

Mixtures in accordance with the following table B are prepared by dissolving the compounds indicated in xylene or Solvesso®100 (s. example C1):

TABLE B

Mixtures of compounds of the formula I and compounds of the formula II; amounts in parts by weight (pbw)

| Compound of the formula I | Compound of the formula II | No. |
|---|---|---|
| 1 pbw I/1 | 1 pbw mixture of II/1 and II/2 | B1 |
| 1 pbw I/1 | 1 pbw II/3 | B2 |
| 1 pbw mixture of I/2 + I/3 | 1 pbw mixture of II/1 and II/2 | B3 |
| 1 pbw mixture of I/2 + I/3 | 1 pbw II/3 | B4 |
| 1 pbw mixture of I/4 + I/5 | 1 pbw mixture of II/1 and II/2 | B5 |
| 1 pbw mixture of I/4 + I/5 | 1 pbw. II/3 | B6 |
| 1 pbw I/6 | 1 pbw mixture of II/1 and II/2 | B7 |
| 1 pbw I/6 | 1 pbw II/3 | B8 |
| 1 pbw I/7 | 1 pbw mixture of II/1 and II/2 | B9 |
| 1 pbw I/7 | 1 pbw II/3 | B10 |
| 3 pbw I/1 | 1 pbw mixture of II/1 and II/2 | B11 |
| 3 pbw I/1 | 1 pbw II/3 | B12 |
| 3 pbw mixture of I/2 + I/3 | 1 pbw mixture of II/1 and II/2 | B13 |
| 3 pbw mixture of I/2 + I/3 | 1 pbw II/3 | B14 |
| 3 pbw mixture of I/4 + I/5 | 1 pbw mixture of II/1 and II/2 | B15 |
| 3 pbw mixture of I/4 + I/5 | 1 pbw II/3 | B16 |
| 3 pbw I/6 | 1 pbw mixture of II/1 and lI/2 | B17 |
| 3 pbw I/6 | 1 pbw II/3 | B18 |
| 3 pbw I/7 | 1 pbw mixture of II/1 and II/2 | B19 |
| 3 pbw I/7 | 1 pbw II/3 | B20 |
| 1 pbw I/1 | 3 pbw mixture of II/1 and II/2 | B21 |
| 1 pbw I/1 | 3 pbw II/3 | B22 |
| 1 pbw mixture of I/2 + I/3 | 3 pbw mixture of II/1 and II/2 | B23 |
| 1 pbw mixture of I/2 + I/3 | 3 pbw II/3 | B24 |
| 1 pbw mixture of I/4 + I/5 | 3 pbw mixture of II/1 and II/2 | B25 |
| 1 pbw mixture of I/4 + I/5 | 3 pbw II/3 | B26 |
| 1 pbw I/6 | 3 pbw mixture of II/1 and II/2 | B27 |
| 1 pbw I/6 | 3 pbw II/3 | B28 |
| 1 pbw I/7 | 3 pbw mixture of II/1 and II/2 | B29 |
| 1 pbw I/7 | 3 pbw II/3 | B30 |
| 1 pbw I/1 | 1 pbw II/4 | B31 |
| 1 pbw mixture of I/2 + I/3 | 1 pbw II/4 | B32 |
| 1 pbw mixture of I/4 + I/5 | 1 pbw II/4 | B33 |
| 1 pbw I/6 | 1 pbw II/4 | B34 |
| 1 pbw I/7 | 1 pbw II/4 | B35 |
| 3 pbw I/1 | 1 pbw II/4 | B36 |
| 3 pbw mixture of I/2 + I/3 | 1 pbw II/4 | B37 |

TABLE B-continued

Mixtures of compounds of the formula I and compounds of the formula II; amounts in parts by weight (pbw)

| Compound of the formula I | Compound of the formula II | No. |
|---|---|---|
| 3 pbw mixture of I/4 + I/5 | 1 pbw II/4 | B38 |
| 3 pbw I/6 | 1 pbw II/4 | B39 |
| 3 pbw I/7 | 1 pbw II/4 | B40 |
| 1 pbw I/1 | 3 pbw II/4 | B41 |
| 1 pbw mixture of I/2 + I/3 | 3 pbw II/4 | B42 |
| 1 pbw mixture of I/4 + I/5 | 3 pbw II/4 | B43 |
| 1 pbw I/6 | 3 pbw lI/4 | B44 |
| 1 pbw I/7 | 3 pbw II/4 | B45 |
| 2 pbw I/1 | 1 pbw mixture of II/1 and II/2 | B46 |
| 2 pbw I/1 | 1 pbw II/3 | B47 |
| 2 pbw mixture of I/2 + I/3 | 1 pbw mixture of II/1 and II/2 | B48 |
| 2 pbw mixture of I/2 + I/3 | 1 pbw II/3 | B49 |
| 2 pbw mixture of I/4 + I/5 | 1 pbw mixture of II/1 and II/2 | B50 |
| 2 pbw mixture of I/4 + I/5 | 1 pbw II/3 | B51 |
| 2 pbw I/6 | 1 pbw mixture of II/1 and II/2 | B52 |
| 2 pbw I/6 | 1 pbw II/3 | B53 |
| 2 pbw I/7 | 1 pbw mixture of II/1 and II/2 | B54 |
| 2 pbw I/7 | 1 pbw II/3 | B55 |
| 2 pbw I/1 | 1 pbw II/4 | B56 |
| 2 pbw mixture of I/2 + I/3 | 1 pbw II/4 | B57 |
| 2 pbw mixture of I/4 + I/5 | 1 pbw II/4 | B58 |
| 2 pbw I/6 | 1 pbw II/4 | B59 |
| 2 pbw I/7 | 1 pbw II/4 | B60 |
| 1 pbw. I/1 | 1 pbw. II/5 | B61 |
| 1 pbw. mixture of I/2 + I/3 | 1 pbw. II/5 | B62 |
| 1 pbw. mixture of I/4 + I/5 | 1 pbw. II/5 | B63 |
| 1 pbw. I/6 | 1 pbw. II/5 | B64 |
| 1 pbw. I/7 | 1 pbw. II/5 | B65 |
| 3 pbw. I/1 | 1 pbw. II/5 | B66 |
| 3 pbw. mixture of I/2 + I/3 | 1 pbw. II/5 | B67 |
| 3 pbw. mixture of I/4 + I/5 | 1 pbw. II/5 | B68 |
| 3 pbw. I/6 | 1 pbw. II/5 | B69 |
| 3 pbw. I/7 | 1 pbw. II/5 | B70 |
| 1 pbw. I/1 | 3 pbw. II/5 | B71 |
| 1 pbw. mixture of I/2 + I/3 | 3 pbw. II/5 | B72 |
| 1 pbw. mixture of I/4 + I/5 | 3 pbw. II/5 | B73 |
| 1 pbw. I/6 | 3 pbw. II/5 | B74 |
| 1 pbw. I/7 | 3 pbw. II/5 | B75 |
| 1 pbw. I/8 | 1 pbw. mixture of II/1 und II/2 | B76 |
| 1 pbw. I/8 | 1 pbw. II/3 | B77 |
| 1 pbw. I/8 | 1 pbw. II/4 | B78 |

TABLE B-continued

Mixtures of compounds of the formula I and compounds of the formula II; amounts in parts by weight (pbw)

| Compound of the formula I | Compound of the formula II | No. |
|---|---|---|
| 1 pbw. I/8 | 1 pbw. II/5 | B79 |
| 3 pbw. I/8 | 1 pbw. mixture of II/1 und II/2 | B80 |
| 3 pbw. I/8 | 1 pbw. II/3 | B81 |
| 3 pbw. I/8 | 1 pbw. II/4 | B82 |
| 3 pbw. I/8 | 1 pbw. II/5 | B83 |
| 1 pbw. I/8 | 3 pbw. mixture of II/1 und II/2 | B84 |
| 1 pbw. I/8 | 3 pbw. II/3 | B85 |
| 1 pbw. I/8 | 3 pbw. II/4 | B86 |
| 1 pbw. I/8 | 3 pbw. II/5 | B87 |
| 1 pbw. I/9 | 1 pbw. mixture of II/1 und II/2 | B88 |
| 1 pbw. I/9 | 1 pbw. II/3 | B89 |
| 1 pbw. I/9 | 1 pbw. II/4 | B90 |
| 1 pbw. I/9 | 1 pbw. II/5 | B91 |
| 3 pbw. I/9 | 1 pbw. mixture of II/1 und II/2 | B92 |
| 3 pbw. I/9 | 1 pbw. II/3 | B93 |
| 3 pbw. I/9 | 1 pbw. II/4 | B94 |
| 3 pbw. I/9 | 1 pbw. II/5 | B95 |
| 1 pbw. I/9 | 3 pbw. mixture of II/1 und II/2 | B96 |
| 1 pbw. I/9 | 3 pbw. II/3 | B97 |
| 1 pbw. I/9 | 3 pbw. II/4 | B98 |
| 1 pbw. I/9 | 3 pbw. II/5 | B99 |
| 1 pbw. I/10 | 1 pbw. mixture of II/1 und II/2 | B100 |
| 1 pbw. I/10 | 1 pbw. II/3 | B101 |
| 1 pbw. I/10 | 1 pbw. II/4 | B102 |
| 1 pbw. I/10 | 1 pbw. II/5 | B103 |
| 3 pbw. I/10 | 1 pbw. mixture of II/1 und II/2 | B104 |
| 3 pbw. I/10 | 1 pbw. II/3 | B105 |

TABLE B-continued

Mixtures of compounds of the formula I and compounds of the formula II; amounts in parts by weight (pbw)

| Compound of the formula I | Compound of the formula II | No. |
|---|---|---|
| 3 pbw. I/10 | 1 pbw. II/4 | B106 |
| 3 pbw. I/10 | 1 pbw. II/5 | B107 |
| 1 pbw. I/10 | 3 pbw. mixture of II/1 und II/2 | B108 |
| 1 pbw. I/10 | 3 pbw. II/3 | B109 |
| 1 pbw. I/10 | 3 pbw. II/4 | B110 |
| 1 pbw. I/10 | 3 pbw. II/5 | B111 |

The mixtures of compounds of the same type (mixtures of compounds of the formula I or mixtures of compounds of the formula II) are technical mixtures and are partly obtained from commercial mixtures of educts.

C) Use Examples

EXAMPLE C1

Stabilizing a 2-coat metallic paint

The novel stabilizer mixtures are tested in a clearcoat having the following composition:

| | |
|---|---|
| Synthacryl ® SC 303[1] | 27.51 |
| Synthacryl ® SC 370[2] | 23.34 |
| Maprenal ® 650[3] | 27.29 |
| butyl acetate/butanol (37/8) | 4.33 |
| isobutanol | 4.87 |
| Solvesso ® 150[4] | 2.72 |
| Kristallöl K-30[5] | 8.74 |
| levelling assistant Baysilon ® MA[6] | 1.20 |
| | 100.00 g |

[1] acrylate resin from Hoechst AG; 65% solution in xylene/butanol 26:9
[2] acrylate resin from Hoechst AG; 75% solution in Solvesso 100[4]
[3] melamine resin from Hoechst AG; 55% solution in isobutanol
[4] aromatic hydrocarbon mixture, boiling range 182–203° C. (Solvesso 150) or 161–178° C. (Solvesso 100); manufacturer: ESSO
[5] aliphatic hydrocarbon mixture, boiling range 145–200° C.; manufacturer: Shell
[6] 1% in Solvesso 150[4]; manufacturer: Bayer AG 1.5% of the mixture to be tested is added in a solution in about 5–10 g of Solvesso®100 to the clearcoat, based on the solids content of the paint. The coating formulations are additionally admixed with 0.7% by weight, based on the solids content of the paint, of a costabilizer (compound C) of the formula (Compound C)

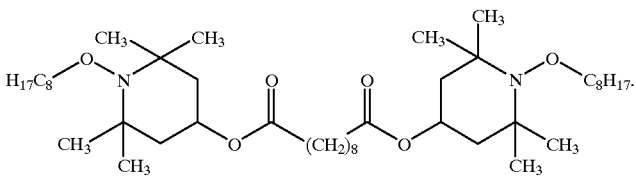

The comparison used is a clearcoat containing no light stabilizer and a clearcoat stabilized using the individual components; the corresponding results are marked in the tables below with an asterisk (*).

The clearcoat is diluted to spray viscosity with Solvesso®1 00 and applied to a prepared aluminium panel (coil coat, filler, silver metallic or blue metallic basecoat) and the painted panel is baked at 1 30° C for 30 minutes. This gives a clearcoat dry-film thickness of 40–50 μm.

The samples are then subjected to weathering in an UVCON® weathering device from Atlas Corp. (UVB-313 lamps) with a cycle of 8 h of UV irradiation at 70° C. and 4 h of condensation at 50° C. Further samples are subjected to natural weathering (Florida, 5° south, SAE J-1976).

The surface gloss (20° gloss in accordance with DIN 67530) and the colour change (ΔE in accordance with DIN 6174) of the samples are measured at regular intervals.

The results are compiled in Tables C1 and C2 below. All amounts are based on the solids content of the clearcoat.

TABLE C1

Gloss retention (DIN 67530) of the
clearcoat over silver metallic basecoat

| Mixture | | | 20° gloss after | |
|---|---|---|---|---|
| No. | Stabilizer I | Stabilizer II | 0 h | 4400 h natural weather |
| * | — | — | 90 | cracking |
| * | — | 1.5% II/1 + II/2 | 91 | 48 |
| * | 1.5% I/2 + I/3 | — | 92 | 48 |
| * | 1.5% I/6 | — | 91 | 28 |
| B3 | 0.75% I/2 + I/3 | 0.75% II/1 + II/2 | | |
| B1 | 0.75% I/1 | 0.75% II/1 + II/2 | | |
| B5 | 0.75% I/4 + I/5 | 0.75% II/1 + II/2 | | |
| B7 | 0.75% I/6 | 0.75% II/1 + II/2 | 91 | 55 |
| B9 | 0.75% I/7 | 0.75% II/1 + II/2 | | |
| B48 | 0.75% I/2 + I/3 | 0.37% II/1 + II/2 | 91 | 69 |
| B17 | 1.12% I/6 | 0.37% II/1 + II/2 | 91 | 60 |
| B32 | 0.75% I/2 + I/3 | 0.75% II/4 | 92 | 78 |
| B31 | 0.75% I/1 | 0.75% II/4 | 91 | 66 |
| B34 | 0.75% I/6 | 0.75% II/4 | | |

*: Comparison

TABLE C2

Color change (ΔE acc. to DIN 6174);
clearcoat over blue metallic basecoat

| Mixture | | | ΔE after | |
|---|---|---|---|---|
| No. | Stabilizer I | Stabilizer II | 3600 h | natural weathering |
| * | — | — | cracking after 1200 h | |
| * | — | 1.5% II/1 + II/2 | 1.5 | |
| * | 1.5% I/6 | — | 1.8 | |
| * | 1.5% I/7 | — | 1.5 | |
| B3 | 0.75% I/2 + I/3 | 0.75% II/1 + II/2 | 1.1 | |
| B1 | 0.75% I/1 | 0.75% II/1 + II/2 | | |
| B5 | 0.75% I/4 + I/5 | 0.75% II/1 + II/2 | 1.0 | |
| B7 | 0.75% I/6 | 0.75% II/1 + II/2 | 1.2 | |
| B9 | 0.75% I/7 | 0.75% II/1 + II/2 | 1.4 | |
| B48 | 0.75% I/2 + I/3 | 0.37% II/1 + II/2 | | |
| B17 | 1.12% I/6 | 0.37% II/1 + II/2 | 1.1 | |
| B32 | 0.75% I/2 + I/3 | 0.75% II/4 | | |
| B31 | 0.75% I/1 | 0.75% II/4 | | |
| B34 | 0.75% I/6 | 0.75% II/4 | 1.2 | |

*: Comparison

The smaller the colour change value, the better the stabilization. The samples stabilized in accordance with the invention exhibit better weathering stability (gloss and colour retention) than comparison samples.

What is claimed is:

1. A mixture comprising a compound of the formula I

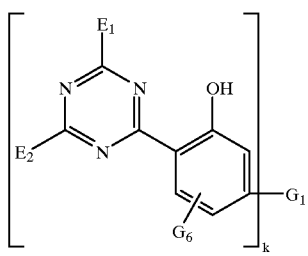

(I)

and a compound of the formula II

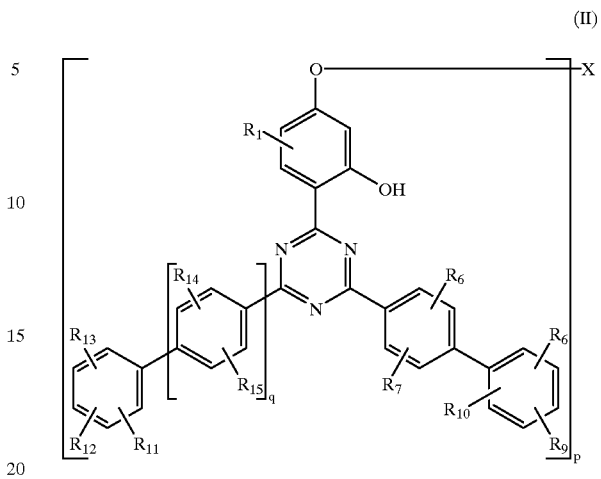

(II)

in which, in formula I $G_1$ hydrogen or —OG; k is 1 or 2; and, if k=1, $E_1$ and $E_2$, independently of one another are a group of the formula Ia or Ib

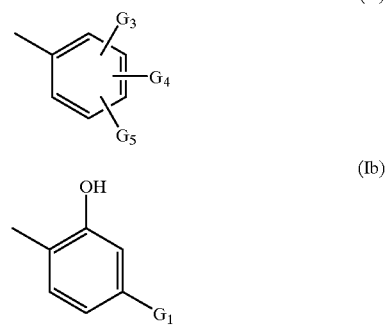

and G is hydrogen or $C_1$–$C_{18}$alkyl; or is $C_1$–$C_{18}$alkyl which is substituted by OH, $C_1$–$C_{18}$alkoxy, $C_5$–$C_{12}$cycloalkoxy, allyloxy, halogen, =O, —COOH, —COO$G_8$, —CONH$_2$, —CONH$G_9$, —CON($G_9$)($G_{10}$), —NH$_2$, —NH$G_9$, =N$G_9$, —N($G_9$)($G_{10}$), —NHCO$G_{11}$, —CN, —OCO$G_{11}$, phenoxy, and/or $C_1$–$C_{18}$alkyl-, $C_1$–$C_{18}$alkoxy- or halo-substituted phenoxy; or G is $C_3$–$C_{50}$alkyl which is interrupted by —O—and can be substituted by OH; or G is $C_3$–$C_6$alkenyl; glycidyl; $C_5$–$C_{12}$cycloalkyl; $C_5$–$C_{12}$cycloalkyl substituted by OH, $C_1$–$C_4$alkyl or —OCO$G_{11}$; $C_7$–$C_{11}$phenylalkyl which is unsubstituted or substituted by OH, Cl, $C_1$–$C_{18}$alkoxy or $C_1$–$C_{18}$alkyl; —CO—$G_{12}$ or —SO$_2$—$G_{13}$;

$G_3$, $G_4$ and $G_5$, independently of one another are H, $C_1$–$C_{12}$alkyl; $C_2$–$C_6$alkenyl; $C_1$–$C_{18}$alkoxy; $C_5$–$C_{12}$cycloalkoxy; $C_2$–$C_{18}$alkenoxy; halogen; —C≡N; $C_1$–$C_4$haloalkyl; $C_7$–$C_{11}$phenylalkyl; COO$G_8$; CONH$_2$; CONH$G_9$; CON$G_9G_{10}$; sulfo; $C_2$–$C_{18}$acylamino; OCO$G_{11}$; phenyloxy; or phenyloxy, $C_1$–$C_{12}$alkyl or $C_1$–$C_{18}$alkoxy each of which is substituted by $C_1$–$C_{18}$alkyl, $C_1$–$C_{18}$alkoxy or halogen; and one radical $G_3$ in formula I additionally embraces the meaning —N$G_{16}G_{17}$; $G_6$ embraces the meanings set out below for $R_1$ in formula II; $G_8$ is $C_1$–$C_{18}$alkyl; $C_3$–$C_{18}$alkenyl; $C_3$–$C_{50}$alkyl which is interrupted by O, NH, N$G_9$ or S and/or is substituted by OH; $C_1$–$C_4$alkyl which is substituted by —P(O)(O$G_{14}$)$_2$, —N($G_9$)($G_{10}$) or —OCO$G_{11}$ and/or OH; glycidyl; $C_5$–$C_{12}$cycloalkyl;

$C_1$–$C_4$alkylcyclohexyl; phenyl; $C_7$–$C_{14}$alkylphenyl; $C_6$–$C_{15}$bicycloalkyl; $C_6$–$C_{15}$bicycloalkenyl; $C_6$–$C_{15}$tricycloalkyl; $C_6$–$C_{15}$bicycloalkylalkyl; or $C_7$–$C_{11}$phenylalkyl; $G_9$ and $G_{10}$ independently of one another are $C_1$–$C_{12}$alkyl; $C_3$–$C_{12}$alkoxyalkyl; $C_2$–$C_{18}$alkanoyl; $C_4$–$C_{16}$dialkylaminoalkyl or $C_5$–$C_{12}$cycloalkyl; or $G_9$ and $G_{10}$ together are $C_3$–$C_9$alkylene or -oxaalkylene or -azaalkylene; $G_{11}$ is $C_1$–$C_{18}$alkyl; $C_1$–$C_{12}$alkoxy; $C_2$–$C_{18}$alkenyl; $C_7$–$C_{11}$phenylalkyl; $C_7$–$C_{11}$phenylalkoxy; $C_6$–$C_{12}$cycloalkyl; $C_6$–$C_{12}$cycloalkoxy; phenoxy or phenyl; or is $C_3$–$C_{50}$alkyl which is interrupted by —O— and can be substituted by OH; $G_{12}$ is $C_1$–$C_{18}$alkyl; $C_2$–$C_{18}$alkenyl; phenyl; $C_1$–$C_{18}$alkoxy; $C_3$–$C_{18}$alkenyloxy; $C_3$–$C_{50}$alkoxy which is interrupted by O, NH, $NG_9$ or S and/or is substituted by OH; cyclohexyloxy; phenoxy; $C_7$–$C_{14}$alkylphenoxy; $C_7$–$C_{11}$phenylalkoxy; $C_1$–$C_{12}$akylamino; phenylamino; tolylamino or naphthylamino; $G_{13}$ is $C_1$–$C12$alkyl; phenyl; naphthyl or $C_7$–$C_{14}$alkylphenyl; $G_{14}$ is $C_1$–$C_{12}$alkyl, methylphenyl or phenyl; $G_{16}$ is hydrogen or $C_1$–$C_{20}$alkyl; $G_{17}$ is hydrogen, $C_1$–$C_{20}$alkyl, $C_7$–$C_{13}$phenylalkyl, —C(=O)—$G_{19}$, —C(=O)—NH—$G_{16}$; $G_{19}$ is $C_1$–$C_{20}$akyl; $C_2$–$C_{20}$alkyl which is interrupted by 1 to 6 oxygen atoms and/or is substituted by OH, halogen, $NH_2$, $NHG_9$ or $NG_9G_{10}$; $C_1$–$C_{20}$alkoxy; phenyl; $C_7$–$C_{13}$phenylalkyl or $C_2$–$C_{20}$alkenyl;

and, if k=2, $E_1$ and $E_2$ are a group of the formula Ia; G is $C_2$–$C_{16}$alkylene, $C_4$–$C_{12}$alkenylene, xylylene, $C_3$–$C_{20}$alkylene which is interrupted by 0 and/or substituted by OH, or a group of the formula —$CH_2CH(OH)CH_2O$—$G_{20}$—$OCH_2CH(OH)CH_2$—, —CO—$G_{21}$—CO—, —CO—NH—$G_{22}$—NH—CO—, —$(CH_2)_j$—COO—$G_{20}$—OOC—$(CH_2)_j$—, in which j is a number from the range from 1 to 3, or is

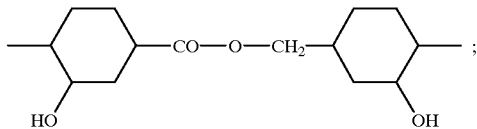

$G_{20}$ is $C_2$–$C_{10}$alkylene; $C_4$–$C_{50}$alkylene which is interrupted by O, phenylene, or a group -phenylene-E-phenylene-, in which E is —O—, —S—, —$SO_2$—, —$CH_2$—, —CO—, or —$C(CH_3)_2$—; $G_{21}$ is $C_2$–$C_{10}$alkylene, $C_2$–$C_{10}$oxaalkylene, $C_2$–$C_{10}$thiaalkylene, $C_6$–$C_7$arylene or $C_2$–$C_6$alkenylene; $G_{22}$ is $C_2$–$C_{10}$alkylene, phenylene, tolylene, diphenylenemethane or a group of the formula

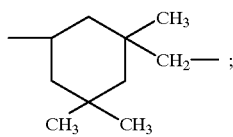

and the remaining radicals embrace the meanings indicated if k=1; and in which, in formula II, $R_1$ is hydrogen; $C_1$–$C_{24}$alkyl or $C_5$–$C_{12}$cycloalkyl; or is $C_1$–$C_{24}$alkyl or $C_5$–$C_{12}$cycloalkyl, each of which is substituted by 1 to 9 halogen atoms, —$R_4$—, —$OR_5$, —$N(R_5)_2$, =$NR_5$, =O, —$CON(R_5)_2$, —$COR_5$, —$COOR_5$, —$OCOR_5$, —$OCON(R_5)_2$, —CN, —$NO_2$, —$SR_5$, —$SOR_5$, —$SO_2R_5$, —$P(O)(OR_5)_2$, a morpholinyl, piperidinyl, 2,2,6,6-tetramethylpiperidinyl, piperazinyl or N-methylpiperazinyl group or by combinations thereof; or is $C_5$–$C_{12}$cycloalkyl or $C_1$–$C_{24}$alkyl which is interrupted by 1 to 6 phenylene, —O—, —$NR_5$—, —$CONR_5$—, —COO—, —OCO—, —$CH(R_5)$—, —$C(R_5)_2$- or -CO- groups or combinations thereof; or $R_1$ is $C_2$–$C_{24}$alkenyl; halogen; —$SR_3$, $SOR_3$; $SO_2R_3$; —$SO_3H$; or $SO_3M$;

$R_3$ is $C_1$–$C_{20}$alkyl; $C_3$–$C_{18}$alkenyl; $C_5$–$C_{12}$cycloalkyl; $C_7$–$C_{15}$phenylalkyl, or $C_6$–$C_{12}$aryl which is unsubstituted or substituted by from 1 to 3 $C_1$–$C_4$alkyl;

$R_4$ is unsubstituted $C_6$–$C_{12}$aryl; or is $C_6$–$C_{12}$aryl substituted by 1 to 3 halogen atoms, $C_1$–$C_8$alkyl or $C_1$–$C_8$alkoxy or combinations thereof; $C_5$–$C_{12}$cycloalkyl; unsubstituted $C_7$–$C_{15}$-phenylalkyl; or is $C_7$–$C_{15}$phenyl alkyl which is substituted in the phenyl ring by 1 to 3 halogen atoms, $C_1$–$C_8$alkyl, $C_1$–$C_8$alkoxy or combinations thereof; or is $C_2$–$C_8$alkenyl;

$R_5$ is $R_4$; hydrogen; $C_1$–$C_{24}$alkyl; or a radical of the formula

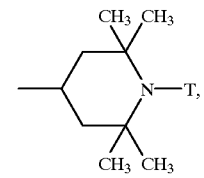

(1a)

in which

T is hydrogen; $C_1$–$C_8$alkyl; $C_2$–$C_8$alkyl which is substituted by hydroxyl or acyloxy; oxyl; hydroxyl; —$CH_2CN$; $C_1$–$C_{18}$alkoxy; $C_5$–$C_{12}$cycloalkoxy; $C_3$–$C_6$alkenyl; $C_7$–$C_9$phenylalkyl; $C_7$–$C_9$phenylalkyl which is substituted once, twice or three times in the phenyl ring by $C_1$–$C_4$alkyl; or is aliphatic $C_1$–$C_8$alkanoyl;

$R_6$ to $R_{15}$, independently of one another are hydrogen; hydroxyl; —C≡N; $C_1$–$C_{20}$alkyl; $C_1$–$C_{20}$alkoxy; $C_7$–$C_{20}$phenylalkyl; $C_4$–$C_{12}$cycloalkyl; $C_4$–$C_{12}$cycloalkoxy; halogen; halo-$C_1$–$C_5$alkyl; sulfonyl; carboxyl; acylamino; acyloxy; $C_1$–$C_{12}$alkoxycarbonyl; aminocarbonyl; —O—Y; or —O—Z; or $R_8$ and $R_9$ together with the phenyl radical, are a cyclic radical which is interrupted by one or more oxygen or nitrogen atoms; and $R_{11}$, if q is 0, additionally comprises the meaning -$NG_{16}G_{17}$, where $G_{16}$ and $G_{17}$ have the meanings defined above;

M is alkali metal;

p is 1 or 2;

q is 0 or1;

and if p=1,

X, Y and Z, independently of one another are $R_y$; $C_1$–$C_{24}$alkyl substituted by $R_x$; $C_2$–$C_{50}$alkyl which is interrupted by oxygen and is substituted by $R_x$; $C_4$–$C_{12}$cycloalkyl substituted by $R_x$; $C_4$–$C_{12}$cycloalkyl substituted by -$OR_y$; $C_4$–$C_{20}$alkenyl interrupted by oxygen; or a radical of one of the formulae —CH$((CH_2)_n$—R)—CO—O—$(CH_2)_m$—$R'_2$;

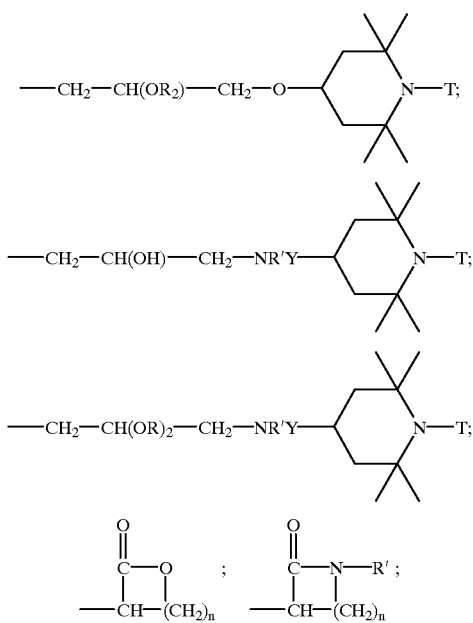

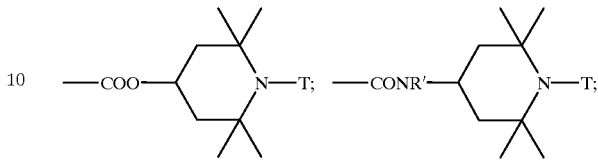

—CO—(CH₂)ₙ—R₂; —CO—O—(CH₂)ₙ—R₂; —CH₂—CH(—O—(CO)—R₂)—R'₂; —CO—NR'—(CH₂)ₙ—R₂;

R₂ and R'₂, independently of one another, if attached to a carbon atom, are Rₓ; and, if attached to an atom other than carbon, are Rᵧ;

n is 0 to 20; and m is 0 to 20; and if p=2,

Y and Z, independently of one another have the same meaning as for p=1; and

X is C₂–C₁₂alkylene; —CO—(C₂–C₁₂alkylene)—CO—; —CO-phenylene-CO—; CO-biphenylene-CO—; CO—O—(C₂–C12alkylene)—O—CO—; —CO—O-phenylene-O—CO—; —CO—O-biphenylene-O—CO—; —CO—NR'—(C₂–C₁₂alkylene)-NR'—CO—; —CO—NR'-phenylene-NR'—CO—; —CO—NR'-biphenylene-NR'—CO—; —CH₂—CH(OH)—CH₂—; —CH₂—CH(OR₂)—CH₂—; —CH₂—CH(OH)—CH₂—O—D—O—CH₂—CH(OH)—CH₂; —CH((CH₂)ₙR₂)—COO—D—OOC—CH((CH₂)ₙR₂)—; —CH₂—CH(OR₂)—CH₂—O—D—O—CH₂—CH(OR₂)—CH₂—;

D is C₂–C₁₂alkylene; C₄–C₅₀alkylene which is interrupted by oxygen; phenylene; biphenylene or phenylene-E-phenylene;

E is —O—; —S—; —SO₂—; —CH₂—; —CO—; or —C(CH₃)₂—;

Rₓ is hydrogen; hydroxyl; C₁–C₂₀alkyl; C₄–C₁₂cycloalkyl; C₁–C₂₀alkoxy; C₄–C₁₂cycloalkoxy; C₄–C₁₂cycloalkyl or C₄–C₁₂cycloalkyloxy each of which is interrupted by oxygen; C₆–C₁₂aryl; hetero-C₃–C₁₂aryl; —ORᵤ; NHRᵤ; Rᵤ; CONR'R''; allyl; C₂–C₂₀alkenyl; C₄–C₁₂cycloalkenyl; C₄–C₁₂cycloalkenyl which is interrupted by oxygen; C₃–C₂₀alkynyl; or C₆–C₁₂cycloalkynyl; or C₁–C₂₀alkyl, C₂–C₂₀alkoxy or C₄–C₁₂cycloalkyl each of which is substituted by hydroxyl, —NH₂, —NH—C₁–C₈alkyl, —NH—cyclohexyl, —N(C₁–C₈alkyl)₂, dicyclohexylamino, halogen, C₁–C₂₀alkyl, C₁–C₂₀alkoxy, C₄–C₁₂cycloalkyl, C₄–C₁₂cycloalkoxy, C₂–C₂₀alkenyl, C₄–C₁₂cycloalkyl, C₃–C₂₀alkynyl, C₆–C₁₂cycloalkynyl, C₆–C₁₂aryl, acylamino, acyloxy, sulfonyl, carboxyl, (meth)acryloxy, (meth)acrylamino,

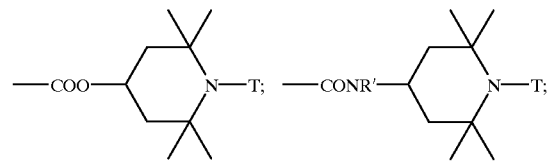

Rᵧ is hydrogen; C₁–C₂₀alkyl; C₄–C₁₂cycloalkyl; C₄–C₁₂cycloalkyl which is interrupted by oxygen; C₆–C₁₂aryl; hetero-C₃–C₁₂ary; Rᵤ; allyl; C₂–C₂₀alkenyl; C₄–C₁₂cycloalkenyl which is uninterrupted or is interrupted by oxygen; C₃–C₂₀alkynyl; or C₆–C₁₂cycloalkynyl; or C₁–C₂₀alkyl or C₄–C₁₂cycloalkyl each of which is substituted by hydroxyl, —NH₂, —NH—C₁–C₈alkyl, —NH-cyclohexyl, -N(C₁–C₈alkyl)₂, dicyclohexylamino, halogen, C₁–C₂₀alkyl, C₁–C₂₀alkoxy, C₄–C₁₂cycloalkyl, C₄–C₁₂cycloalkoxy, C₂–C₂₀alkenyl, C₄–C₁₂cycloalkyl, C₃–C₂₀alkynyl, C₆–C₁₂cycloalkynyl, C₆–C₁₂aryl, acylamine, acyloxy, sulfonyl, carboxyl, (meth)acryloxy, (meth)acrylamino,

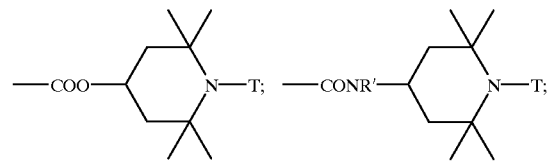

Rᵤ is —COR'; —COOR'; —CONR'R''; —CO—CH=CH₂; —CO—C(CH₃)=CH₂;

R' and R'', independently of one another are hydrogen; C₁–C₂₀alkyl; C₄–C₅₀alkyl which is interrupted by oxygen; C₄–C₁₂cycloalkyl; C₄–C₁₂cycloalkyl which is interrupted by oxygen; C₂–C₂₀alkenyl; C₂–C₂₀alkenyl which is interrupted by oxygen; or are C₆–C₁₂aryl; or are C₁–C₂₀alkyl or C₄–C₁₂cycloalkyl each of which substituted by hydroxyl, —NH₂, —NH—C₁–C₈alkyl, —NH-cyclohexyl, —N(C₁–C₈alkyl)₂, dicyclohexylamino, halogen, C₁–C₂₀alkyl, C₁–C₂₀alkoxy, C₄–C₁₂cycloalkyl, C₄–C₁₂cycloalkoxy, C₂–C₂₀alkenyl, C₄–C₁₂cycloalkyl, C₃–C₂₀alkynyl, C₆–C₁₂cycloalkynyl, C₆–C₁₂aryl, acylamino, acyloxy, sulfonyl, carboxyl, (meth)acryloxy, (meth)acrylamino,

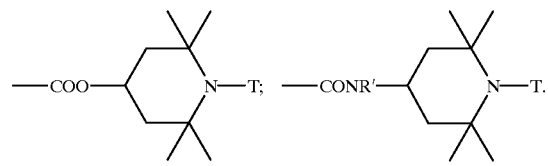

2. A mixture according to claim 1, comprising instead of a compound of the formula I a compound of the formula I'

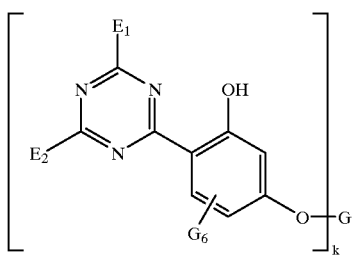

(I')

and in which in formula I'k is 1 or 2; and, if k=1, $E_1$ and $E_2$, independently of one another are a group of the formula I$a$ or I'$b$

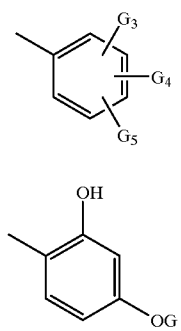

(Ia)

(I'b)

and G is hydrogen or $C_1$–$C_{18}$alkyl; or is $C_1$–$C_{18}$alkyl which is substituted by OH, $C_1$–$C_{18}$alkoxy, allyloxy, halogen, =O, —COOH, —COOG$_8$, —CONH$_2$, —CONHG$_9$, —CON(G$_9$) (G$_{10}$), —NH$_2$, —NHG$_9$, =NG$_9$, —N(G$_9$)(G$_{10}$), —NHCOG$_{11}$, —CN, —OCOG$_{11}$, phenoxy and/or $C_1$–$C_{18}$alkyl-, $C_1$–$C_{18}$alkoxy- or halo-substituted phenoxy; or G is $C_3$–$C_{50}$alkyl which is interrupted by —O—; or G is $C_3$–$C_{50}$alkyl which is interrupted by —O— and substituted by OH; or G is $C_3$–$C_6$alkenyl; glycidyl; $C_5$–$C_{12}$cycloalkyl; $C_5$–$C_{12}$cycloalkyl substituted by OH, $C_1$–$C_4$-alkyl or —OCOG$_{11}$; $C_7$–$C_{11}$phenylalkyl which is unsubstituted or substituted by OH, Cl, $C_1$–$C_{18}$alkoxy or $C_1$–$C_{18}$alkyl; —CO—G$_{12}$ or —SO$_2$—G$_{,3}$; $G_3$, $G_4$ and $G_5$, independently of one another are H, $C_1$–$C_{12}$alkyl; $C_2$–$C_6$alkenyl; $C_1$–$C_{18}$alkoxy; $C_5$–$C_{12}$cycloalkoxy; $C_2$–$C_{18}$alkenoxy; halogen; —C≡N; $C_1$–$C_4$haloalkyl; $C_7$–$C_{11}$phenylalkyl; COOG$_8$; CONGH$_2$; CONHG$_9$; CONG$_9$G$_{10}$ ; sulfo; $C_2$–$C_{18}$acylamino; OCOG$_{11}$; phenyloxy; or phenyloxy, $C_1$–$C_{12}$alkyl or $C_1$–$C_{18}$alkoxy which is substituted by $C_1$–$C_{18}$alkyl, $C_1$–$C_{18}$alkoxy or halogen; $G_6$ embraces the meanings set out below for $R_1$ in formula II; $G_8$ is $C_1$–$C_{18}$alkyl; $C_2$–$C_{18}$alkenyl; $C_3$–$C_{50}$alkyl which is interrupted by O, NH, NG$_9$ or S and/or is substituted by OH; $C_1$–$C_4$alkyl which is substituted by —P(O)(OG$_{14}$)$_2$, —N(G$_9$)(G$_{10}$) or —OCOG$_{11}$ and/or OH; glycidyl; cyclohexyl; phenyl; $C_7$–$C_{14}$alkylphenyl or $C_7$–$C_{11}$phenylalkyl; $G_9$ and $G_{10}$ independently of one another are $C_1$–$C_{12}$alkyl; $C_3$–$C_{12}$alkoxyalkyl; $C_2$–$C_{18}$alkanoyl; $C_4$–$C_{16}$dialkylaminoalkyl or $C_5$–$C_{12}$cycloalkyl; or $G_9$ and $G_{10}$ together are $C_3$–$C_9$alkylene or -oxaalkylene or -azaalkylene; $G_{11}$ is $C_1$–$C_{18}$alkyl; $C_2$–$C_{18}$alkenyl or phenyl; or is $C_3$–$C_{50}$alkyl which is interrupted by —O—; or is $C_3$–$C_{50}$alkyl which is interrupted by —O— and substituted by OH; $G_{12}$ is $C_1$–$C_{18}$alkyl; $C_2$–$C_{18}$alkenyl; phenyl; $C_1$–$C_{18}$alkoxy; $C_3$–$C_{18}$alkenyloxy; $C_3$–$C_{50}$alkoxy which is interrupted by O, NH, NG$_9$ or S and/or is substituted by OH; cyclohexyloxy; phenoxy; $C_7$–$C_{14}$alkylphenoxy; $C_7$–$C_{11}$phenylalkoxy; $C_1$–$C_{12}$alkylamino; phenylamino; tolylamino or naphthylamino; $G_{13}$ is $C_1$–$C_{12}$alkyl; phenyl; naphthyl or $C_7$–$C_{14}$alkylphenyl; $G_{14}$ is $C_1$–$C_{12}$alkyl, methylphenyl or phenyl; and, if k=2 $E_1$ and $E_2$ are a group of the formula I$a$; G is $C_2$–$C_{16}$alkylene, $C_4$–$C_{12}$alkenylene, xylylene, $C_3$–$C_{20}$alkylene which is interrupted by O and/or substituted by OH, or a group of the formulae —CH$_2$CH (OH)CH$_2$O—G$_{20}$—OCH$_2$CH(OH)CH$_2$—, —CO—G$_{21}$—CO—, —CO—NH—G$_{22}$—NH—CO—, —(CH$_2$)$_j$—COO—G$_{23}$—OOC—(CH$_2$)$_j$—, in which j is a number from the range from 1 to 3, or is

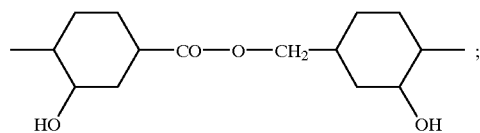

$G_{20}$ is $C_2$–$C_{10}$alkylene; $C_4$–$C_{50}$alkylene which is interrupted by O, phenylene, or a group -phenylene-E-phenylene-, in which E is —O—, —S—, —SO$_2$—, —CH$_2$—, —CO—, or —C(CH$_3$)$_2$—; $G_{21}$ is $C_2$–$C_{10}$alkylene, $C_2$–$C_{10}$oxaalkylene, $C_2$–$C_{10}$thiaalkylene, $C_6$–$C_{12}$arylene or $C_2$–$C_6$alkenylene; $G_{22}$ is $C_2$–$C_{10}$alkylene, phenylene, tolylene, diphenylenemethane or a group of the formula

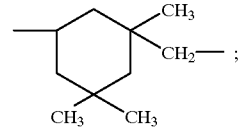

$G_{23}$ is $C_2$–$C_{10}$alkylene or $C_4$–$C_{20}$alkylene which is interrupted by O; and the remaining radicals embrace the meanings indicated for k=1;

and in which, in formula II, $R_1$ is hydrogen; $C_1$–$C_{24}$alkyl or $C_5$–$C_{12}$cycloalkyl; or is $C_1$–$C_{24}$alkyl or $C_5$–$C_{12}$cycloalkyl each of which is substituted by 1 to 9 halogen atoms, —R$_4$, —OR$_5$, —N(R$_5$)$_2$, =NR$_5$, =O, —CON(R$_5$)$_2$, —COR$_5$, —COOR$_5$, —OCOR$_5$, —OCON(R$_5$)$_2$, —CN, —NO$_2$, —SR$_5$, —SOR$_5$, —SO$_2$R$_5$ , —P(O)(OR$_5$)$_2$, a morpholinyl, piperidinyl, 2,2,6,6-tetramethylpiperidinyl, piperazinyl- or N-methylpiperazinyl group or by combinations thereof; or is $C_5$–$C_{12}$cycloalkyl or $C_1$–$C_{24}$alkyl each of which is interrupted by 1 to 6 phenylene, —O—, —NR$_5$—, —CONR$_5$—, —COO—, —OCO—, —CH(R$_5$)—, —C(R$_5$)$_2$— or —CO—groups or combinations thereof; or $R_1$ is $C_2$–$C_{24}$alkenyl; halogen; —SR$_3$, SOR$_3$; SO$_2$R$_3$; —SO$_3$H; or SO$_3$M;

$R_3$ is $C_1$–$C_{20}$alkyl; $C_3$–$C_{18}$alkenyl; $C_5$–$C_{12}$cycloalkyl; $C_7$–$C_{15}$phenylalkyl; or $C_6$–C12aryl which is unsubstituted or substituted by from 1 to 3 $C_1$–$C_4$alkyl;

$R_4$ is unsubstituted $C_6$–$C_{12}$aryl; or is $C_6$–$C_{12}$aryl substituted by 1 to 3 halogen atoms, $C_1$–$C_8$alkyl or $C_1$–$C_8$alkoxy or combinations thereof; $C_5$–$C_{12}$cycloalkyl; unsubstituted $C_7$–$C_{15}$-phenylalkyl; $C_7$–$C_{15}$phenylalkyl which is substituted in the phenyl ring by 1 to 3 halogen atoms, $C_1$–$C_8$alkyl, $C_1$–$C_8$alkoxy or combinations thereof; or is $C_2$–$C_8$alkenyl;

$R_5$ is $R_4$; hydrogen, $C_1$–$C_{24}$alkyl; or a radical of the formula

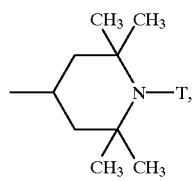

(1a)

wherein

T is hydrogen; $C_1$–$C_8$alkyl; $C_2$–$C_8$alkyl which is substituted by hydroxyl or by acyloxy; oxyl; hydroxyl; —$CH_2CN$; $C_1$–$C_{18}$alkoxy; $C_5$–$C_{12}$cycloalkoxy; $C_3$–$C_6$alkenyl; $C_7$–$C_9$phenylalkyl; $C_7$–$C_9$phenylalkyl which is substituted once, twice or three times in the phenyl ring by $C_1$–$C_4$alkyl; or is aliphatic $C_1$–$C_8$alkanoyl;

$R_6$ to $R_{15}$, independently of one another are hydrogen; hydroxyl; —C≡N; $C_1$–$C_{20}$alkyl; $C_1$–$C_{20}$alkoxy; $C_7$–$C_{20}$phenylalkyl; $C_4$–$C_{12}$cycloalkyl; $C_4$–$C_{12}$cycloalkoxy; halogen; halo-$C_1$–$C_5$alkyl; sulfonyl; carboxyl; acylamino; acyloxy; $C_1$–$C_{12}$alkoxycarbonyl; aminocarbonyl; —O—Y; or —O—Z; or $R_8$ and $R_9$ together with the phenyl radical, are a cyclic radical which is interrupted by oxygen or nitrogen;

M is alkali metal;

p is 1 or 2;

q is 0 or 1;

and if p=1,

X, Y and Z, independently of one another are $R_y$; $C_1$–$C_{24}$alkyl substituted by $R_x$; $C_2$–$C_{50}$alkyl which is interrupted by oxygen and is substituted by $R_x$; $C_4$–$C_{12}$cycloalkyl substituted by $R_x$; $C_4$–$C_{12}$cycloalkyl substituted by —$OR_y$; $C_4$–$C_{20}$alkenyl interrupted by oxygen; or a radical of one of the formulae —CH$((CH_2)_n$—$R_2)$—CO—O—$(CH_2)_m$—$R'_2$; —CH$((CH_2)_n$—$R_2)$—CO—(NR')—$(CH_2)_m$—$R'_2$;

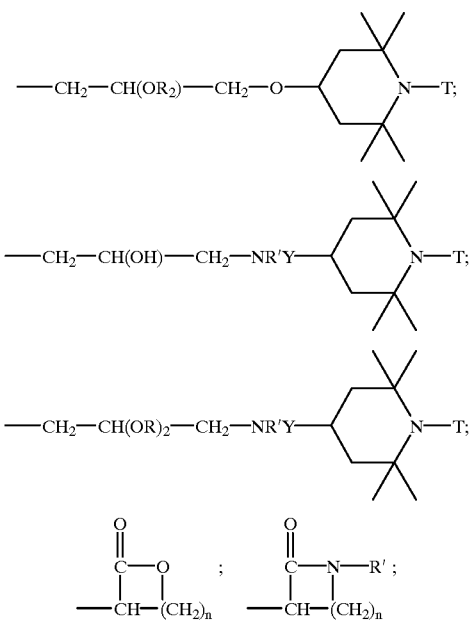

—CO—$(CH_2)_n$—$R_2$; —CO—O—$(CH_2)_n$—$R_2$; —H$_2$—CH$(-O-(CO)-R_2-R'_2$; —CO—NR'—$(CH_2)$—$R_2$;

$R_2$ and $R'_2$ independently of one another, if attached to a carbon atom, are $R_x$; and, if attached to an atom other than carbon, are $R_y$;

n is 0 to 20; and m is 0 to 20; and if p=2,

Y and Z, independently of one another have the same meaning as for p=1; and

X is $C_2$–$C_{12}$alkylene; —CO—($C_2$—$C_{12}$alkylene)—CO—; —CO-phenylene-CO—; —CO-biphenylene-CO—; CO—O—($C_2$—$C_{12}$alkylene)—O—CO—; —CO—O-phenylene-O—CO—; —CO—O-biphenylene-O—CO—; —CO—NR'—($C_2$–$C_{12}$alkylene)—NR'—CO—; —CO—NR'-phenylene-NR'—CO—; —CO—NR'-biphenylene-NR'—CO—; —$CH_2$—CH(OH) —$CH_2$—; —$CH_2$—CH($OR_2$) —$CH_2$—; —$CH_2$—CH(OH)—$CH_2$—O—D—O—$CH_2$—CH(OH)—$CH_2$; —$CH_2$—CH($OR_2$)—$CH_2$—O—D—O—$CH_2$—CH($OR_2$)—$CH_2$—;

D is $C_2$–$C_{12}$alkylene; $C_4$–$C_{50}$alkylene which is interrupted by oxygen; phenylene; biphenylene or phenylene-E-phenylene;

E is —O—; —S—; —$SO_2$—; —$CH_2$—; —CO—; or —C($CH_3$)$_2$—;

$R_x$ is hydrogen; hydroxyl; $C_1$–$C_{20}$akyl; $C_4$–$C_{12}$cycloalkyl; $C_1$–$C_{20}$alkoxy; $C_4$–$C_{12}$cycloalkoxy; $C_4$–$C_{12}$cycloalkyl or $C_4$–$C_{12}$cycloalkyloxy each of which is interrupted by oxygen; $C_6$–$C_{12}$aryl; hetero-$C_3$–$C_{12}$aryl; —$OR_z$; $NHR_z$; $R_z$; $CONR'R''$; allyl; $C_2$–$C_{20}$alkenyl; $C_4$–$C_{12}$cycloalkenyl; $C_4$–$C_{12}$cycloalkenyl which is interrupted by oxygen; $C_3$–$C_{20}$alkynyl; or $C_6$–$C_{12}$cycloalkynyl;

$R_y$ is hydrogen; $C_1$–$C_{20}$alkyl; $C_4$–$C_{12}$cycloalkyl; $C_4$–$C_{12}$cycloalkyl which is interrupted by oxygen; $C_6$–$C_{12}$aryl; hetero-$C_3$–$C_{12}$alryl; $R_z$; allyl; $C_2$–$C_{20}$alkenyl; $C_4$–$C_{12}$cycloalkenyl which is uninterrupted or is interrupted by oxygen; $C_3$–$C_{20}$alkynyl; or $C_6$–$C_{12}$cycloalkynyl;

$R_z$ is —COR'; —COOR'; —CONR'R''; —CO—CH=$CH_2$; —CO—C($CH_3$)=$CH_2$; R' and R'', independently of one another are hydrogen; $C_1$–$C_{20}$alkyl; $C_4$–$C_{50}$alkyl which is interrupted by oxygen; $C_4$–$C_{12}$cycloalkyl; $C_4$–$C_{12}$cycloalkyl which is interrupted by oxygen; $C_2$–$C_{20}$alkenyl; $C_2$–$C_{20}$alkenyl which is interrupted by oxygen; or are $C_6$–$C_{12}$aryl.

3. A mixture according to claim 1 comprising from 0.2 to 5 parts by weight of compound of the formula II per part by weight of compound of the formula I.

4. A mixture according to claim 1, in which in the compound of the formula I G if k=1, is hydrogen, $C_1$–$C_{18}$alkyl, allyl, glycidyl or benzyl; or is $C_1$–$C_{12}$alkyl which is substituted by OH, $C_1$–$C_{18}$alkoxy, $C_5$–$C_{12}$cycloalkoxy, phenoxy, —$COOG_8$, —$CONHG_9$, —$CON(G_9)(G_{10})$ and/or —$OCOG_{11}$; or G is —$(CH_2CHG_{15}$—O)$_i$—$G_{18}$ or —$CH_2$—CH(OH)—$CH_2$—O—$(CH_2CHG_{15}$—O)$_i$—$G_{18}$ where i is a number from the range 1–12; G, if k=2, is $C_2$–$C_{16}$alkylene, $C_4$–$C_{12}$alkenylene, xylylene, or is $C_3$–$C_{20}$alkylene interrupted by 0 and/or substituted by OH; $G_3$, $G_4$ and $G_5$, independently of one another are H, $C_1$–$C_{12}$alkyl, $C_2$–$C_6$alkenyl, $C_1$–$C_{12}$alkoxy, Cl, F; and one radical $G_3$ in formula I additionally comprises $NG_{16}G_{17}$; $G_6$ is hydrogen, $C_1$–$C_{24}$alkyl, $C_5$–$C_{12}$cycloalkyl or $C_7$–$C_{15}$phenylalkyl; $G_8$ is $C_1$–$C_{12}$alkyl; $C_3$–$C_{18}$alkenyl; $C_3$–$C_{20}$alkyl which is interrupted by O and/or substituted by OH; $C_5$–$C_{12}$cycloalkyl; $C_1$–$C_4$alkylcyclohexyl; or is $C_1$–$C_4$alkyl substituted by —P(O)(OG$_{14}$)$_2$; G$_9$ and G$_{10}$, independently of one another are $C_1$–$C_8$alkyl or cyclohexyl; or G$_9$ and G$_{10}$ together are pentamethylene or 3-oxapentamethylene; G$_{11}$ is $C_1$–$C_8$alkyl, $C_2$–$C_5$alkenyl, cyclohexyl or phenyl; or is $C_3$–$C_{20}$alkyl which is interrupted by —O—; or is $C_3$–$C_{20}$alkyl which is interrupted by —O— and substituted by OH; and G$_{14}$ is $C_1$–$C_4$alkyl; G$_1$ is H or methyl; G$_{16}$ is hydrogen; G$_{17}$ is hydrogen, $C_1$–$C_{20}$alkyl, CO—G$_{19}$; G$_{18}$ is H, $C_1$–$C_{18}$alkyl, phenyl or $C_7$–$C_{11}$alkylphenyl; and G$_{19}$ is $C_1$–$C_{20}$alkyl; $C_2$–$C_{20}$alkenyl; $C_1$–$C_{20}$alkoxy; or $C_2$–$C_{20}$akyl which is interrupted by O; and in which in the compound of the formula II $R_1$ is hydrogen; $C_1$–$C_{24}$alkyl, $C_5$–$C_{12}$cycloalkyl or $C_7$–$C_{15}$phenylalkyl;

$R_6$ to $R_{15}$, independently of one another are H, $C_1$–$C_{12}$alkyl, $C_2$–$C_6$alkenyl, Cl, F, OY or OZ;

p is 1; and q is 0 or 1;

X, Y and Z, independently of one another are $R_y$; $C_1$–$C_{24}$alkyl which is substituted by $R_x$; $C_2$–$C_{50}$alkyl which is interrupted by one or more oxygen atoms and substituted by $R_x$; or are a radical of one of the formulae —CH((CH$_2$)$_n$—R$_2$—CO—O—(CH$_2$)$_m$—R'$_2$; —CH((CH$_2$)$_n$—R$_2$)—CO—(NR')—(CH$_2$)$_m$—R'$_2$; —CO—(CH$_2$)$_n$—R$_2$; —CO—O—(CH$_2$)$_n$—R$_2$; —CH$_2$—CH(—O—(CO)—R$_2$)—R'$_2$; —CO—NR'—(CH$_2$)$_n$—R$_2$;

R$_2$ and R'$_2$, independently of one another, if attached to a carbon atom, are $R_x$; and, if attached to an atom other than carbon, are $R_y$;

n is 0 to 20; and m is 0 to 20; and $R_x$ is hydrogen; hydroxyl; $C_1$–$C_{20}$alkyl; $C_4$–$C_{12}$cycloalkyl; $C_1$–$C_{20}$alkoxy; $C_6$–$C_{12}$cycloalkoxy; phenyl; —OR$_z$; NHR$_z$; R$_z$; allyl; or $C_1$–$C_{20}$alkyl, $C_2$–$C_{20}$alkoxy or $C_4$–$C_{12}$cycloalkyl, each of which is substituted by hydroxyl, $C_1$–$C_{20}$alkyl, $C_1$–$C_{20}$alkoxy, acyloxy, carboxyl, or (meth)acryloxy;

$R_y$ is hydrogen; $C_1$–$C_{20}$alkyl; $C_4$–$C_{12}$cycloalkyl; phenyl; R$_z$; allyl; or $C_1$–$C_{20}$alkyl or $C_4$–$C_{12}$cycloalkyl, each of which is substituted by hydroxyl, $C_1$–$C_{20}$alkyl, $C_1$–$C_{20}$alkoxy, acyloxy, carboxyl or (meth)acryloxy;

$R_z$ is —COR'; —COOR'; —CONR'R"; —CO—CH=CH$_2$; —CO—C(CH$_3$)=CH$_2$;

R' and R", independently of one another, are hydrogen; $C_1$–$C_{20}$alkyl; $C_4$–$C_{20}$alkyl which is interrupted by oxygen; $C_4$–$C_{12}$cycloalkyl; $C_2$–$C_3$alkenyl; phenyl; or are $C_1$–$C_{20}$alkyl or cyclohexyl each of which is substituted by hydroxyl, $C_1$–$C_{12}$alkyl, $C_1$–$C_{12}$alkoxy or carboxyl.

5. A mixture according to claim 1 in which in the compound of the formula I k is 1; G is hydrogen; $C_1$–$C_{18}$alkyl; $C_1$–$C_{12}$alkyl substituted by OH, $C_1$–$C_{18}$alkoxy, $C_5$–$C_{12}$cycloalkoxy, —COOG$_8$, —CON(G$_9$)(G$_{10}$), phenoxy and/or —OCOG$_{11}$; glycidyl or benzyl; or G is —(CH$_2$CHG$_{15}$—O)$_i$—G$_{18}$ or —CH$_2$—CH(OH)—CH$_2$—O—(CH$_2$CHG$_{15}$—O)$_i$—G$_{18}$ where i is a number in the range 2–12; G$_8$ is $C_1$–$C_{12}$alkyl; $C_3$–$C_{12}$alkenyl; $C_6$–$C_{20}$alkyl which is interrupted by O and/or substituted by OH; $C_5$–$C_{12}$cycloalkyl; $C_1$–$C_4$alkylcyclohexyl; or $C_1$–$C_4$alkyl which is substituted by —P(O)(OG$_{14}$)$_2$; G$_9$ and G$_{10}$ are $C_4$–$C_8$alkyl; G$_{11}$ is $C_1$–$C_8$alkyl, cyclohexyl or $C_2$–$C_3$alkenyl; or is $C_3$–$C_{20}$alkyl which is interrupted by —O—; or is $C_3$–$C_{20}$alkyl which is interrupted by —O— and substituted by OH; G$_{14}$ is $C_1$–$C_4$alkyl; G$_{15}$ is hydrogen; and G$_{18}$ is H, $C_1$–$C_{18}$alkyl, phenyl or $C_1$–$C_{10}$alkylphenyl; and in which in the compound of the formula II R$_6$ to R$_{15}$, independently of one another are H, $C_1$–$C_{12}$alkyl, Cl and R$_{11}$, R$_{12}$ and R$_{13}$ if q is 0, additionally embrace OH and OY;

p is 1;

X and Y, independently of one another, are R$_y$; $C_2$–$C_{12}$alkyl which is substituted by R$_x$; $C_3$–$C_{30}$alkyl which is interrupted by oxygen and substituted by R$_x$;

$R_x$ is hydroxyl; $C_1$–$C_{12}$alkyl; $C_6$–$C_{12}$cycloalkyl; $C_1$–$C_{20}$alkoxy; $C_6$–$C_{12}$cycloalkoxy; phenyl; —OR$_z$; R$_z$; allyl; or is $C_1$–$C_{20}$alkyl, $C_2$–$C_{20}$alkoxy or cyclohexyl each of which is substituted by hydroxyl, $C_1$–$C_{12}$alkyl, $C_1$–$C_{12}$alkoxy or carboxyl;

$R_y$ is hydrogen; $C_1$–$C_{12}$alkyl; $C_6$–$C_{12}$cycloalkyl; phenyl; R$_z$; allyl; or $C_1$–$C_{20}$alkyl or cyclohexyl each of which is substituted by hydroxyl, $C_1$–C12alkyl, $C_1$–$C_{12}$alkoxy or carboxyl;

$R_z$ is —COR'; —COOR'; —CONR'R"; —CO—CH=CH$_2$; —CO—C(CH$_3$)=CH$_2$; R' and R", independently of one another, are hydrogen; $C_1$–$C_{20}$alkyl; $C_4$–$C_{20}$alkyl which is interrupted by oxygen; $C_4$–$C_{12}$cycloalkyl; or are $C_2$–$C_{20}$alkyl or cyclohexyl each of which is substituted by hydroxyl, $C_1$–$C_{12}$alkyl, $C_1$–$C_{12}$alkoxy or carboxyl.

6. A mixture according to claim 1 in which in the compound of the formula I k is 1;

G$_3$, G$_4$ and G$_5$, independently of one another are H, Cl, $C_1$–$C_8$alkyl, allyl or $C_1$–$C_4$alkoxy; G$_6$ is hydrogen; G is $C_1$–$C_{18}$-alkyl or benzyl; or is $C_2$–$C_6$alkyl substituted by OH, $C_1$–$C_{18}$alkoxy, phenoxy and/or —OCOG$_{11}$; or is $C_1$–$C_6$alkyl substituted by —COOG$_8$; G$_8$ is $C_1$–$C_8$alkyl or $C_3$–$C_8$alkenyl; and G$_{11}$ is $C_1$–$C_4$alkyl or $C_2$–$C_3$alkenyl; and in which in the compound of the formula II R$_6$ to R$_{15}$ are H;

q is 1;

p is 1;

X and Y, independently of one another, are R$_y$; $C_2$–$C_{12}$alkyl which is substituted by R$_x$; $C_3$–$C_{30}$alkyl which is interrupted by oxygen and substituted by R$_x$;

$R_x$ is hydroxyl; $C_1$–$C_{20}$alkoxy; cyclohexyloxy; —OR$_z$; R$_z$; allyl;

$R_y$ is hydrogen; $C_1$–$C_{20}$alkyl; cyclohexyl;

$R_z$ is —COR'; —COOR';

R' is hydrogen; $C_1$–$C_{20}$alkyl; $C_4$–$C_{20}$alkyl which is interrupted by oxygen; cyclohexyl or $C_1$–$C_4$alkylcyclohexyl.

7. A composition comprising
A) an organic material sensitive to damage by light, oxygen and/or heat, and
B) as stabilizer, a mixture comprising a compound of the formula I and a compound of the formula II.

8. A composition according to claim 7, comprising from 0.01 to 15 parts by weight of component B per 100 parts by weight of component A.

9. A composition according to claim 7, comprising in addition to components A and B another stabilizer or other additive.

10. A composition according to claim 7, comprising as component A a synthetic organic polymer.

11. A composition according to claim 7, comprising as component A a thermoplastic polymer, a binder for coatings or a photographic material.

12. A composition according to claim 11, comprising as component A a binder for coatings and as further component a stabilizer selected from the group consisting of light stabilizers of the sterically hindered amine and/or 2-hydroxyphenyl-2H-benzotriazole type.

13. A composition according to claim 12, which is an automotive topcoat.

14. A composition according to claim 12, which is a powder coating.

15. A method of stabilizing organic material against damage by light, oxygen and/or heat, which comprises adding to said material as stabilizer a mixture according to claim 1 comprising a compound of the formula I and a compound of the formula II.

* * * * *